(12) United States Patent
Koutrouli et al.

(10) Patent No.: US 12,225,350 B2
(45) Date of Patent: Feb. 11, 2025

(54) HEARING DEVICE AND A HEARING SYSTEM COMPRISING A MULTITUDE OF ADAPTIVE TWO CHANNEL BEAMFORMERS

(71) Applicant: Oticon A/S, Smørum (DK)

(72) Inventors: Eleni Koutrouli, Mölndal (SE); Michael Syskind Pedersen, Smørum (DK); Jesper Jensen, Smørum (DK); Jan M. De Haan, Smørum (DK)

(73) Assignee: OTICON A/S, Smørum (DK)

( * ) Notice: Subject to any disclaimer, the term of this patent is extended or adjusted under 35 U.S.C. 154(b) by 0 days.

(21) Appl. No.: 18/405,455

(22) Filed: Jan. 5, 2024

(65) Prior Publication Data

US 2024/0155297 A1  May 9, 2024

Related U.S. Application Data

(60) Continuation of application No. 18/084,209, filed on Dec. 19, 2022, now Pat. No. 11,917,370, which is a
(Continued)

(30) Foreign Application Priority Data

Sep. 27, 2018  (EP) .................................. 18197069

(51) Int. Cl.
*H04R 1/40* (2006.01)
*H04R 25/00* (2006.01)
*A61N 1/36* (2006.01)

(52) U.S. Cl.
CPC ......... *H04R 25/407* (2013.01); *H04R 25/405* (2013.01); *H04R 25/604* (2013.01);
(Continued)

(58) Field of Classification Search
CPC ..... H04R 1/406; H04R 25/405; H04R 25/407
See application file for complete search history.

(56) References Cited

U.S. PATENT DOCUMENTS 7,471,798 B2   12/2008  Warren
9,301,049 B2    3/2016  Elko et al.
(Continued)

FOREIGN PATENT DOCUMENTS

DE   10310579 A1   9/2004
DE   10331956 B3   1/2005
EP    3413589 A1  12/2018

OTHER PUBLICATIONS

Buechner et al. "Advanced Beamformers for Cochlear Implant Users: Acute Measurement of Speech Perception in Challenging Listening Conditions" PLOS ONE, vol. 9, No. 4, Apr. 22, 2014, p. e95542.

(Continued)

*Primary Examiner* — Ryan Robinson
(74) *Attorney, Agent, or Firm* — Birch, Stewart, Kolasch & Birch, LLP

(57) ABSTRACT

A binaural hearing system comprises first and second hearing aids, each comprising antenna and transceiver circuitry allowing the exchange of audio signals between them and a BTE-part adapted for being located at or behind the external ear (pinna) of the user and comprising front and rear input transducers providing respective front and rear electric input signals. Each of the hearing aids comprises primary and secondary adaptive 2-channel beamformers each providing a spatially filtered signal based on first and second beamformer-input signals. The primary and secondary 2-channel beamformers are coupled in a cascaded structure. The inputs to the primary 2-channel beamformers are, locally generated, front and rear electric input signals. The inputs to the secondary 2-channel beamformer may be beamformed signals from the first and second hearing aids respectively. The spatially filtered signal of the secondary 2-channel beamformer may comprise an estimate of a target signal in the environment of the user.

16 Claims, 11 Drawing Sheets

Related U.S. Application Data division of application No. 17/565,034, filed on Dec. 29, 2021, now Pat. No. 11,564,043, which is a division of application No. 17/106,453, filed on Nov. 30, 2020, now Pat. No. 11,252,515, which is a division of application No. 16/584,668, filed on Sep. 26, 2019, now Pat. No. 10,887,703.

(52) U.S. Cl.
CPC .......... *A61N 1/36038* (2017.08); *H04R 25/55* (2013.01); *H04R 2225/021* (2013.01); *H04R 2225/55* (2013.01); *H04R 2225/67* (2013.01)

(56) References Cited

U.S. PATENT DOCUMENTS

| | | | |
|---|---|---|---|
| 9,472,180 B2* | 10/2016 | Olsson | G10K 11/175 |
| 9,716,944 B2* | 7/2017 | Yliaho | H04R 3/005 |
| 10,262,676 B2* | 4/2019 | Olsson | H04M 1/6058 |
| 10,425,745 B1* | 9/2019 | Merks | H04R 3/005 |
| 2004/0240683 A1 | 12/2004 | Niederdrank | |
| 2005/0041824 A1 | 2/2005 | Arndt et al. | |
| 2012/0082322 A1* | 4/2012 | van Waterschoot | H04S 7/30 381/92 |
| 2015/0172807 A1 | 6/2015 | Olsson | |
| 2019/0253813 A1* | 8/2019 | Pedersen | H04R 25/405 |

OTHER PUBLICATIONS

European Communication pursuant to Article 94(3) EPC for European Application No. 19198561.3, dated Apr. 4, 2023.

* cited by examiner

HEARING DEVICE AND A HEARING SYSTEM COMPRISING A MULTITUDE OF ADAPTIVE TWO CHANNEL BEAMFORMERS

This application is a Continuation of application Ser. No. 18/084,209, filed Dec. 19, 2022, which is a Divisional of Application Ser. No. 17/565,034, filed on Dec. 29, 2021, now U.S. Pat. No. 11,564,043, issued Jan. 24, 2023, which is a Divisional of Application Ser. No. 17/106,453, filed on Nov. 30, 2020, now U.S. Pat. No. 11,252,515, issued Feb. 15, 2022, which is a Divisional of Application Ser. No. 16/584,668, filed on Sep. 26, 2019, now U.S. Pat. No. 10,887,703, issued Jan. 5, 2021, which claims priority under 35 U.S.C. § 119(a) to European Patent Application No. EP 18197069.0 filed on Sep. 27, 2018, all of which are hereby expressly incorporated by reference into the present application.

SUMMARY

The present disclosure deals with audio processing devices or systems, e.g. hearing aids, headsets, speakerphones or the like, and possible auxiliary devices associated therewith, e.g. with which exchange of data can be established.

An audio processing system may comprise at least two or at least three input transducers configured to convert sound in the environment of the audio processing system, to respective at least three electric input signals, one of which being selected as a reference input transducer providing a reference input signal, or a reference input signal being defined by an electric signal determined from said at least three electric input signals as if provided by a microphone located at a spatial reference point relative to locations of said at least three input transducers. The at least two adaptive 2-channel beamformers, may each provide a spatially filtered signal based on first and second beamformer-input signals, wherein said adaptive 2-channel beamformers maintain unit amplitude and phase for a target component of said reference input signal. The at least two 2-channel beamformers may be coupled in a cascaded structure at least comprising a primary layer and a secondary layer. The primary layer may comprise at least one of the at least two 2-channel beamformers, said at least one 2-channel beamformer of the primary layer being termed primary 2-channel beamformer(s). The secondary layer may comprise at least another one of said at least two 2-channel beamformers, said at least one 2-channel beamformer of the second layer being termed secondary 2-channel beamformer(s). The at least two 2-channel beamformers may comprise a A) first primary 2-channel beamformer, wherein said first beamformer-input signal is said reference input signal, and wherein said second beamformer-input signal is selected among the remaining electric input signals, said first primary 2-channel beamformer providing a primary spatially filtered reference signal; and B) a first secondary 2-channel beamformer, wherein said first beamformer-input signal is said primary spatially filtered reference signal, and wherein said second beamformer-input signal is selected among a) those of said at least three electric input signals, which are not used as inputs to said first primary 2-channel beamformer, or among said at least two electric input signals, and b) a primary spatially filtered signal from a possible further primary 2-channel beamformer, said first secondary 2-channel beamformer providing a secondary spatially filtered reference signal. An adaptive parameter of a given 2-channel beamformer may be determined from the first and second beamformer-input signals for said 2-channel beamformer.

A Hearing System:

In an aspect, the present disclosure deals with hearing devices, e.g. hearing aids, headsets, speakerphones or the like, and possible auxiliary devices associated therewith, e.g. with which exchange of data can be established.

In an aspect of the present application, a hearing system comprising a first hearing device, e.g. a hearing aid, the first hearing device being configured to be worn at or in a first ear of a user, or to be fully or partially implanted in the head of the user at the first ear is provided. The hearing system comprises at least three input transducers configured to convert sound in the environment of the hearing system to respective at least three electric input signals, one of which being selected as a reference input transducer providing a reference input signal, or a reference input signal being defined by an electric signal determined from said at least three electric input signals as if provided by a microphone located at a spatial reference point relative to locations of said at least three input transducers;

at least two adaptive 2-channel beamformers, each providing a spatially filtered signal based on first and second beamformer-input signals, wherein said adaptive 2-channel beamformers maintain unit amplitude and phase for a target component of said reference input signal;

said at least two 2-channel beamformers being coupled in a layered structure at least comprising a primary layer and a secondary layer, where said primary layer comprises at least one of said at least two 2-channel beamformers, termed primary 2-channel beamformer(s); and wherein said secondary layer comprises at least another one of said at least two 2-channel beamformers, termed secondary 2-channel beamformer(s).

The at least two 2-channel beamformers may comprise a first primary 2-channel beamformer, wherein said first beamformer-input signal is said reference input signal, and wherein said second beamformer-input signal is selected among the remaining electric input signals, said first primary 2-channel beamformer providing a primary spatially filtered reference signal; and a first secondary 2-channel beamformer, wherein said first beamformer-input signal is said primary spatially filtered reference signal, and wherein said second beamformer-input signal is selected among a) those of said at least three electric input signals, which are not used as inputs to said first primary 2-channel beamformer, and b) a primary spatially filtered signal from a possible further primary 2-channel beamformer, said first secondary 2-channel beamformer providing a secondary spatially filtered reference signal, and wherein an adaptive parameter of a given 2-channel beamformer is determined from the first and second beamformer-input signals for said 2-channel beamformer.

Thereby an improved hearing system may be provided.

The adaptive parameter of a given 2-channel beamformer may be determined (e.g. solely) from the first and second beamformer-input signals for the 2-channel beamformer in question.

An advantage of the hearing system according to the present disclosure is that the adaptive 2-channel beamformers maintain unit amplitude and phase for a target component of said reference input signal, so that noise reduction is performed with an unchanged target direction. The direction to the target sound source as experienced at the reference input (e.g. at the reference microphone or a virtual reference microphone) is maintained through the cascaded 2-channel beamformer structure (so that target signal components remain unchanged).

Properties of the virtual microphone (virtual reference point) may e.g. obtained off-line by measuring the transfer function to a microphone located at the desired (reference) position (which is not a location of a microphone of the final (physically implemented) microphone array) with respect to the other microphones in the microphone array. This is illustrated in FIG. 9.

The main motivation of using multiple 2-input beamformers instead of one M-input beamformers is the reduction in complexity in the adaptation of the β-parameter based on the noise covariance. In a 2-input Generalized Sidelobe Canceller (GSC), the β-parameter is a scalar, defined by $$\beta_{opt} = \frac{w_O^H C_v w_C}{w_C^H C_v w_C},$$

where the division operation between two scalar values has the largest influence on the computational complexity.

In an M>2 GSC, the β-parameter is an (M−1)×1 size vector, defined by $$\beta_{opt} = (W_C^H C_v W_C)^{-1} W_C^H C_v W_O,$$

where $W_C^H$ is known as a size (M−1)×M blocking matrix and $W_O$ is an M×1 beamformer vector. The main influence on the complexity is the (M−1) size matrix inverse operation, which is more expensive than M−1 (e.g. two for M=3) divisions (one division per 2-channel beamformer).

The proposed structure only requires the additional computation complexity of a single division for every extra microphone with 2-input beamformer added in the structure. When using a full GSC, the complexity increases exponentially as a function of the number of microphones: $O((M-1)^3)$.

The first and/or secondary 2-channel beamformers may be implemented as respective minimum variance distortionless response (MVDR) beamformers.

The term 'selected among the remaining electric input signals' is in the present context intended to mean 'selected among the at least three electric input signals, except the reference signal'.

The first primary two-channel beamformer is configured to maintain the target signal component (amplitude/magnitude and phase) picked up by the reference input transducer and provided in the reference signal (and to attenuate noise from other directions than the target signal). The target signal is e.g. provided by a localized sound source, e.g. in the form of a speech signal of a talking person.

The adaptive parameter(s), e.g. a parameter β, e.g. a frequency dependent parameter β(k), where k is a frequency index, of each of the 2-channel beamformers are 'autonomously' determined (i.e. only in dependence of its own first and second beamformer-input signals).

In the present context, the term 'a layered structure of 2-channel beamformers' is taken to mean that the 2-channel beamformers are cascaded, so that outputs of a 2-channel beamformer of a given layer (e.g. the $1^{st}$ (or primary) layer) is used as input to a 2-channel beamformer of a subsequent layer (e.g. the $2^{nd}$ (or secondary) layer). The term 'a layered structure of 2-channel beamformers' may be taken to be equivalent to the term 'a cascaded coupling of 2-channel beamformers'.

The layered structure of 2-channel beamformers may comprise more than two layers, primary, secondary, tertiary, etc., as e.g. indicated in FIG. 3. In a three-layered structure, the secondary spatially filtered reference signal is used as a first beamformer-input signal to a first tertiary 2-channel beamformer, etc.

The hearing system may comprise at least three input transducers, which when worn by the user are located two and two on first, second and third straight lines, which together form a triangle. In this embodiment, the three input transducers are not located on one straight line. At least two of the at least three input transducers may be located on a straight line having an extension in a direction towards a mouth of the user, when wearing the hearing system. Thereby a (primary) 2-channel beamformer with a target direction towards the user's mouth (and thus particularly suitable for picking up the voice of the user (own voice') may be implemented. In an embodiment, at least one, such as two of the (at least) three input transducers are located in a BTE-part of the hearing device adapted to be located at or behind the external ear (pinna) of the user (or in concha). In an embodiment, one of the (at least) three input transducers is(are) located in or at an ear canal of the user (or elsewhere around the ear). This has the advantage of allowing 'out of horizontal plane' beamforming, e.g. directed towards sound coming from above or below the user wearing the hearing device(s). It may as well, however, allow better beamforming in the horizontal plane, even though none of the microphones are located in the horizontal plane. In an embodiment, at least one of the input transducers is located in another device, e.g. separate from the hearing device in question, e.g. in another body worn device, e.g. in a hearing device located at or in the opposite ear of the user, or in a separate microphone unit, e.g. of a communication device (e.g. a smartphone), or a remote control device. The hearing system may be configured to pick up the user's own voice in a particular communication-mode of operation. In this mode of operation, the hearing system may be configured to receive an input audio signal from another device (e.g. a telephone or similar device), e.g. representing a voice of a communication partner.

The hearing system may comprise at least three input transducers, which when worn by the user are located on a straight line. In an embodiment, the three input transducers constitute a linear array having a fixed distance between neighbouring input transducers of the array.

In an embodiment, the hearing system, e.g. the (first) hearing device, comprises just three input transducers.

The hearing system may comprise at least two primary 2-channel beamformers.

The layered structure (cascaded coupling) of the hearing system may comprise at least three 2-channel beamformers, e.g. distributed in respective primary, secondary and tertiary layers.

The hearing system may comprise a second hearing device, e.g. a hearing aid, the second hearing device being configured to be worn at or in a second ear of the user, or to be fully or partially implanted in the head of the user at the second ear, wherein at least one of said at least three input transducers is located in the second hearing device. The first and second hearing devices may each comprise appropriate antenna and transceiver circuitry configured to allow the establishment of a communication link between them exchange information (e.g. audio signals, such as electric input signals from an input transducer) between them. The at least three input transducers of the hearing system may be distributed over the first and second hearing devices. Each of the first and second hearing devices may comprise two or three or more input transducers.

In an embodiment, an input transducer is or comprises a microphone.

The hearing system may comprise a detection unit for determining a sound source location encoding parameter indicative of a location of or a direction of arrival to said target sound source. Identification and location of or a target direction to a target sound source (e.g. a person speaking) can be estimated in a number of ways, cf. e.g. EP3413589A1. The sound source location encoding parameter may e.g. be determined as or based on a covariance estimate between said electric input signals, e.g. two and two, e.g. between each combination two electric input signals selected among the at least three electric input signals of the hearing system. The sound source location encoding parameter may e.g. be determined as or based on a direction of arrival.

The detection unit may be configured to determine the sound source location encoding parameter as, or based on, a covariance estimate between the electric input signals.

The hearing system may comprise a user interface allowing a user to indicate a location of or a direction of arrival to the target sound source. The user interface may e.g. be implemented as an APP of a remote control or a smartphone, or similar body worn device, e.g. a device worn on an arm, e.g. a smartwatch. The hearing system may be configured to extract a sound source location encoding parameter from the indication on the user interface.

The hearing system may comprise a controller for automatically selecting said second beamformer-input signals of the first primary and first secondary 2-channel beamformers, respectively. The second beamformer-input signals may e.g. be selected in dependence of an estimated or expected direction of arrival of a target signal component of the sound in the environment.

The hearing system may be configured to provide that the second beamformer-input signals of the first primary and first secondary 2-channel beamformers, respectively, are determined from the sound source location encoding parameter or from a user's indication on the user interface.

The hearing system may comprise a memory comprising corresponding values of a) a target sound source location or direction of arrival and b) appropriate coupling configurations of the available input transducers to 2-channel beamformers of the hearing system. The memory may e.g. contain data that allow a selection of an appropriate coupling of electric input signals to the respective primary, secondary, etc., 2-channel beamformers to be made in dependence of the (target) sound source location encoding parameter, e.g. the direction of arrival.

The hearing system may be arranged to provide that the (first and/or second) hearing device is(are) constituted by or comprises a hearing aid, a headset, an earphone, an ear protection device or a combination thereof. The hearing system may comprise a spectacle frame or other carrier. The spectacle frame or other carrier may comprise one or more of the input transducers, e.g. microphones. The input transducers may e.g. be located on one or both side bars, and/or on a cross-bar of the spectacle frame. The spectacle frame may e.g. support glasses to enhance a user's eye sight.

The hearing system may comprise a (first) hearing device and an auxiliary device. The auxiliary device may as well contain a cascaded beamformer according to the present disclosure.

The hearing system may be adapted to establish a communication link between the hearing device or hearing devices and the auxiliary device to provide that information, e.g. control and status signals, and possibly audio signals, can be exchanged or forwarded from one to the other.

The auxiliary device may comprise the user interface.

The 2-channel beamformer may be optimized as a hardware block. The function of a 2-channel beamformer may e.g. be optimized as a standard cell in a component library for a given semiconductor process. This has the advantage that the properties of the 2-channel beamformer can be optimized (e.g. with respect to delay) and easily duplicated in different parts of the hearing system (e.g. in a given (ASIC) processor-circuit of a hearing device or other processing device).

In an embodiment, the hearing system is adapted to establish a communication link between the hearing device and the auxiliary device to provide that information (e.g. control and status signals, possibly audio signals) can be exchanged or forwarded from one to the other.

In an embodiment, the hearing system comprises an auxiliary device, e.g. a remote control, a smartphone, or other portable or wearable electronic device, such as a smartwatch or the like.

In an embodiment, the auxiliary device is or comprises a remote control for controlling functionality and operation of the hearing device(s). In an embodiment, the function of a remote control is implemented in a smartphone, the smartphone possibly running an APP allowing to control the functionality of the hearing system via the smartphone (the hearing device(s) comprising an appropriate wireless interface to the smartphone, e.g. based on Bluetooth or some other standardized or proprietary scheme).

In an embodiment, the auxiliary device is or comprises an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the hearing device.

In an embodiment, the auxiliary device is or comprises another hearing device. In an embodiment, the hearing system comprises two hearing devices adapted to implement a binaural hearing system, e.g. a binaural hearing aid system.

A Hearing Device:

In an embodiment, the hearing device is adapted to provide a frequency dependent gain and/or a level dependent compression and/or a transposition (with or without frequency compression) of one or more frequency ranges to one or more other frequency ranges, e.g. to compensate for a hearing impairment of a user. In an embodiment, the hearing device comprises a signal processor for enhancing the input signals and providing a processed output signal.

In an embodiment, the hearing device comprises an output unit for providing a stimulus perceived by the user as an acoustic signal based on a processed electric signal. In an embodiment, the output unit comprises a number of electrodes of a cochlear implant (for a CI type hearing device) or a vibrator of a bone conducting hearing device. In an embodiment, the output unit comprises an output transducer. In an embodiment, the output transducer comprises a receiver (loudspeaker) for providing the stimulus as an acoustic signal to the user (e.g. in an acoustic (air conduction based) hearing device). In an embodiment, the output transducer comprises a vibrator for providing the stimulus as mechanical vibration of a skull bone to the user (e.g. in a bone-attached or bone-anchored hearing device).

In an embodiment, the hearing device comprises an input unit for providing an electric input signal representing sound. In an embodiment, the input unit comprises an input transducer, e.g. a microphone, for converting an input sound to an electric input signal. In an embodiment, the input unit comprises a wireless receiver for receiving a wireless signal comprising sound and for providing an electric input signal representing said sound.

The hearing device comprises a directional microphone system adapted to spatially filter sounds from the environment, and thereby enhance a target acoustic source among a multitude of acoustic sources in the local environment of the user wearing the hearing device. In an embodiment, the directional system is adapted to detect (such as adaptively detect) from which direction a particular part of the microphone signal originates. This can be achieved in various different ways as e.g. described in the prior art. In hearing devices, a microphone array beamformer is often used for spatially attenuating background noise sources. Many beamformer variants can be found in literature. The minimum variance distortionless response (MVDR) beamformer is widely used in microphone array signal processing. Ideally the MVDR beamformer keeps the signals from the target direction (also referred to as the look direction) unchanged, while attenuating sound signals from other directions maximally. The generalized sidelobe canceller (GSC) structure is an equivalent representation of the MVDR beamformer offering computational and numerical advantages over a direct implementation in its original form.

In an embodiment, the hearing device comprises an antenna and transceiver circuitry (e.g. a wireless receiver) for wirelessly receiving a direct electric input signal from another device, e.g. from an entertainment device (e.g. a TV-set), a communication device, a wireless microphone, or another hearing device. In an embodiment, the direct electric input signal represents or comprises an audio signal and/or a control signal and/or an information signal.

Preferably, communication between the hearing device and the other device is based on some sort of modulation at frequencies above 100 kHz. Preferably, frequencies used to establish a communication link between the hearing device and the other device is below 70 GHz, e.g. located in a range from 50 MHz to 70 GHz, e.g. above 300 MHz, e.g. in an ISM range above 300 MHz, e.g. in the 900 MHz range or in the 2.4 GHz range or in the 5.8 GHz range or in the 60 GHz range (ISM=Industrial, Scientific and Medical, such standardized ranges being e.g. defined by the International Telecommunication Union, ITU). In an embodiment, the wireless link is based on a standardized or proprietary technology. In an embodiment, the wireless link is based on Bluetooth technology (e.g. Bluetooth Low-Energy technology).

In an embodiment, the hearing device is a portable device, e.g. a device comprising a local energy source, e.g. a battery, e.g. a rechargeable battery.

In an embodiment, the hearing device comprises a forward or signal path between an input unit (e.g. an input transducer, such as a microphone or a microphone system and/or direct electric input (e.g. a wireless receiver)) and an output unit, e.g. an output transducer. In an embodiment, the signal processor is located in the forward path. In an embodiment, the signal processor is adapted to provide a frequency dependent gain according to a user's particular needs. In an embodiment, the hearing device comprises an analysis path comprising functional components for analyzing the input signal (e.g. determining a level, a modulation, a type of signal, an acoustic feedback estimate, etc.). In an embodiment, some or all signal processing of the analysis path and/or the signal path is conducted in the frequency domain. In an embodiment, some or all signal processing of the analysis path and/or the signal path is conducted in the time domain.

In an embodiment, an analogue electric signal representing an acoustic signal is converted to a digital audio signal in an analogue-to-digital (AD) conversion process, where the analogue signal is sampled with a predefined sampling frequency or rate $f_s$, $f_s$ being e.g. in the range from 8 kHz to 48 kHz (adapted to the particular needs of the application) to provide digital samples $x_n$ (or x[n]) at discrete points in time $t_n$ (or n), each audio sample representing the value of the acoustic signal at to by a predefined number $N_b$ of bits, $N_b$ being e.g. in the range from 1 to 48 bits, e.g. 24 bits. Each audio sample is hence quantized using $N_b$ bits (resulting in $2^{Nb}$ different possible values of the audio sample). A digital sample x has a length in time of $1/f_s$, e.g. 50 μs, for $f_s$=20 kHz. In an embodiment, a number of audio samples are arranged in a time frame. In an embodiment, a time frame comprises 64 or 128 audio data samples. Other frame lengths may be used depending on the practical application.

In an embodiment, the hearing devices comprise an analogue-to-digital (AD) converter to digitize an analogue input (e.g. from an input transducer, such as a microphone) with a predefined sampling rate, e.g. 20 kHz. In an embodiment, the hearing devices comprise a digital-to-analogue (DA) converter to convert a digital signal to an analogue output signal, e.g. for being presented to a user via an output transducer.

In an embodiment, the hearing device, e.g. the microphone unit, and or the transceiver unit comprise(s) a TF-conversion unit for providing a time-frequency representation of an input signal. In an embodiment, the time-frequency representation comprises an array or map of corresponding complex or real values of the signal in question in a particular time and frequency range. In an embodiment, the TF conversion unit comprises a filter bank for filtering a (time varying) input signal and providing a number of (time varying) output signals each comprising a distinct frequency range of the input signal. In an embodiment, the TF conversion unit comprises a Fourier transformation unit for converting a time variant input signal to a (time variant) signal in the (time-)frequency domain. In an embodiment, the frequency range considered by the hearing device from a minimum frequency $f_{min}$ to a maximum frequency $f_{max}$ comprises a part of the typical human audible frequency range from 20 Hz to 20 kHz, e.g. a part of the range from 20 Hz to 12 kHz. Typically, a sample rate $f_s$ is larger than or equal to twice the maximum frequency $f_{max}$, $f_s \geq 2f_{max}$. In an embodiment, a signal of the forward and/or analysis path of the hearing device is split into a number NI of frequency bands (e.g. of uniform width), where NI is e.g. larger than 5, such as larger than 10, such as larger than 50, such as larger than 100, such as larger than 500, at least some of which are processed individually. In an embodiment, the hearing device is/are adapted to process a signal of the forward and/or analysis path in a number NP of different frequency channels (NP≤NI). The frequency channels may be uniform or non-uniform in width (e.g. increasing in width with frequency), overlapping or non-overlapping.

In an embodiment, the hearing device comprises a number of detectors configured to provide status signals relating to a current physical environment of the hearing device (e.g. the current acoustic environment), and/or to a current state of the user wearing the hearing device, and/or to a current state or mode of operation of the hearing device. Alternatively or additionally, one or more detectors may form part of an external device in communication (e.g. wirelessly) with the hearing device. An external device may e.g. comprise another hearing device, a remote control, and audio delivery device, a telephone (e.g. a smartphone), an external sensor, etc.

In an embodiment, one or more of the number of detectors operate(s) on the full band signal (time domain). In an embodiment, one or more of the number of detectors operate (s) on band split signals ((time-) frequency domain), e.g. in a limited number of frequency bands.

In an embodiment, the number of detectors comprises a level detector for estimating a current level of a signal of the forward path. In an embodiment, the predefined criterion comprises whether the current level of a signal of the forward path is above or below a given (L-)threshold value. In an embodiment, the level detector operates on the full band signal (time domain). In an embodiment, the level detector operates on band split signals ((time-) frequency domain).

In a particular embodiment, the hearing device comprises a voice detector (VD) for estimating whether or not (or with what probability) an input signal comprises a voice signal (at a given point in time). A voice signal is in the present context taken to include a speech signal from a human being. It may also include other forms of utterances generated by the human speech system (e.g. singing). In an embodiment, the voice detector unit is adapted to classify a current acoustic environment of the user as a VOICE or NO-VOICE environment. This has the advantage that time segments of the electric microphone signal comprising human utterances (e.g. speech) in the user's environment can be identified, and thus separated from time segments only (or mainly) comprising other sound sources (e.g. artificially generated noise). In an embodiment, the voice detector is adapted to detect as a VOICE also the user's own voice. Alternatively, the voice detector is adapted to exclude a user's own voice from the detection of a VOICE.

In an embodiment, the hearing device comprises an own voice detector for estimating whether or not (or with what probability) a given input sound (e.g. a voice, e.g. speech) originates from the voice of the user of the system. In an embodiment, a microphone system of the hearing device is adapted to be able to differentiate between a user's own voice and another person's voice and possibly from NON-voice sounds.

In an embodiment, the number of detectors comprises a movement detector, e.g. an acceleration sensor. In an embodiment, the movement detector is configured to detect movement of the user's facial muscles and/or bones, e.g. due to speech or chewing (e.g. jaw movement) and to provide a detector signal indicative thereof.

In an embodiment, the hearing device comprises a classification unit configured to classify the current situation based on input signals from (at least some of) the detectors, and possibly other inputs as well. In the present context 'a current situation' is taken to be defined by one or more of
a) the physical environment (e.g. including the current electromagnetic environment, e.g. the occurrence of electromagnetic signals (e.g. comprising audio and/or control signals) intended or not intended for reception by the hearing device, or other properties of the current environment than acoustic);
b) the current acoustic situation (input level, feedback, etc.), and
c) the current mode or state of the user (movement, temperature, cognitive load, etc.);
d) the current mode or state of the hearing device (program selected, time elapsed since last user interaction, etc.) and/or of another device in communication with the hearing device.

In an embodiment, the hearing device further comprises other relevant functionality for the application in question, e.g. compression, noise reduction, etc.

In an embodiment, the hearing device comprises a listening device, e.g. a hearing aid, e.g. a hearing instrument, e.g. a hearing instrument adapted for being located at the ear or fully or partially in the ear canal of a user, e.g. a headset, an earphone, an ear protection device or a combination thereof. In an embodiment, the hearing assistance system comprises a speakerphone (comprising a number of input transducers and a number of output transducers, e.g. for use in an audio conference situation), e.g. comprising a beamformer filtering unit, e.g. providing multiple beamforming capabilities.

Use:

In an aspect, use of a hearing device as described above, in the 'detailed description of embodiments' and in the claims, is moreover provided. In an embodiment, use is provided in a system comprising audio distribution. In an embodiment, use is provided in a system comprising one or more hearing aids (e.g. hearing instruments), headsets, ear phones, active ear protection systems, etc., e.g. in handsfree telephone systems, teleconferencing systems (e.g. including a speakerphone), public address systems, karaoke systems, classroom amplification systems, etc.

An APP:

In a further aspect, a non-transitory application, termed an APP, is furthermore provided by the present disclosure. The APP comprises executable instructions configured to be executed on an auxiliary device to implement a user interface for a hearing device or a hearing system described above in the 'detailed description of embodiments', and in the claims. In an embodiment, the APP is configured to run on cellular phone, e.g. a smartphone, or on another portable device allowing communication with said hearing device or said hearing system.

The hearing system (including the auxiliary device, and the APP) may be adapted to allow a user to indicate a location of or direction to a target sound source of current interest to the user. Thereby the determination of a currently appropriate (beneficial) coupling configuration of the electric input signals to the cascaded 2-channel beamformers can be facilitated, including a choice of reference input transducer (and corresponding reference input signal). The APP may have access to a database or dictionary (stored in a memory of the hearing system, e.g. of the auxiliary device) of corresponding appropriate reference input transducer and coupling configuration for a number of different locations of or directions to the target sound source (relative to the user).

A Method of Operating an Audio Processing Device or System:

In an aspect of the present application, a method of operating an audio processing device or system, e.g. a hearing device or a hearing system. The method comprises
providing at least three electric input signals representative of sound in the environment of the audio processing device or system, one of which being selected as a reference input providing a reference input signal, or a reference input signal being defined by an electric signal determined from said at least three electric input signals as if provided by an input located at a spatial reference point relative to locations of inputs providing said at least three electric input signals;

providing at least two adaptive 2-channel beamformers, each providing a spatially filtered signal based on first and second beamformer-input signals, wherein said adaptive 2-channel beamformers maintain unit amplitude and phase for a target component of said reference input signal; and providing that said at least two 2-channel beamformers are coupled in a cascaded structure at least comprising a primary layer and a secondary layer, providing that said primary layer comprises at least one of said at least two 2-channel beamformers, said at least one beamformer of the primary layer being termed primary 2-channel beamformer(s); and providing that said secondary layer comprises at least another one of said at least two 2-channel beamformers, said at least one beamformer of the second layer being termed secondary 2-channel beamformer(s).

providing that said at least two adaptive 2-channel beamformers comprise a first primary 2-channel beamformer, wherein said first beamformer-input signal is said reference input signal, and wherein said second beamformer-input signal is selected among the remaining electric input signals, said first primary 2-channel beamformer providing a primary spatially filtered reference signal; and a first secondary 2-channel beamformer, wherein said first beamformer-input signal is said primary spatially filtered reference signal, and wherein said second beamformer-input signal is selected among a) those of said at least three electric input signals, which are not used as inputs to said first primary 2-channel beamformer, and b) a primary spatially filtered signal from a possible further primary 2-channel beamformer, said first secondary 2-channel beamformer providing a secondary spatially filtered reference signal, and determining an adaptive parameter of a given 2-channel beamformer from the first and second beamformer-input signals for said 2-channel beamformer.

It is intended that some or all of the structural features of the device or system described above, in the 'detailed description of embodiments' or in the claims can be combined with embodiments of the method, when appropriately substituted by a corresponding process and vice versa. Embodiments of the method have the same advantages as the corresponding devices or systems.

Definitions:

In the present context, a 'hearing device' refers to a device, such as a hearing aid, e.g. a hearing instrument, or an active ear-protection device, or other audio processing device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A 'hearing device' further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing device may be configured to be worn in any known way, e.g. as a unit arranged behind the ear with a tube leading radiated acoustic signals into the ear canal or with an output transducer, e.g. a loudspeaker, arranged close to or in the ear canal, as a unit entirely or partly arranged in the pinna and/or in the ear canal, as a unit, e.g. a vibrator, attached to a fixture implanted into the skull bone, as an attachable, or entirely or partly implanted, unit, etc. The hearing device may comprise a single unit or several units communicating electronically with each other. The loudspeaker may be arranged in a housing together with other components of the hearing device, or may be an external unit in itself (possibly in combination with a flexible guiding element, e.g. a dome-like element).

More generally, a hearing device comprises an input transducer for receiving an acoustic signal from a user's surroundings and providing a corresponding input audio signal and/or a receiver for electronically (i.e. wired or wirelessly) receiving an input audio signal, a (typically configurable) signal processing circuit (e.g. a signal processor, e.g. comprising a configurable (programmable) processor, e.g. a digital signal processor) for processing the input audio signal and an output unit for providing an audible signal to the user in dependence on the processed audio signal. The signal processor may be adapted to process the input signal in the time domain or in a number of frequency bands. In some hearing devices, an amplifier and/or compressor may constitute the signal processing circuit. The signal processing circuit typically comprises one or more (integrated or separate) memory elements for executing programs and/or for storing parameters used (or potentially used) in the processing and/or for storing information relevant for the function of the hearing device and/or for storing information (e.g. processed information, e.g. provided by the signal processing circuit), e.g. for use in connection with an interface to a user and/or an interface to a programming device. In some hearing devices, the output unit may comprise an output transducer, such as e.g. a loudspeaker for providing an air-borne acoustic signal or a vibrator for providing a structure-borne or liquid-borne acoustic signal. In some hearing devices, the output unit may comprise one or more output electrodes for providing electric signals (e.g. a multi-electrode array for electrically stimulating the cochlear nerve). In an embodiment, the hearing device comprises a speakerphone (comprising a number of input transducers and a number of output transducers, e.g. for use in an audio conference situation).

In some hearing devices, the vibrator may be adapted to provide a structure-borne acoustic signal transcutaneously or percutaneously to the skull bone. In some hearing devices, the vibrator may be implanted in the middle ear and/or in the inner ear. In some hearing devices, the vibrator may be adapted to provide a structure-borne acoustic signal to a middle-ear bone and/or to the cochlea. In some hearing devices, the vibrator may be adapted to provide a liquid-borne acoustic signal to the cochlear liquid, e.g. through the oval window. In some hearing devices, the output electrodes may be implanted in the cochlea or on the inside of the skull bone and may be adapted to provide the electric signals to the hair cells of the cochlea, to one or more hearing nerves, to the auditory brainstem, to the auditory midbrain, to the auditory cortex and/or to other parts of the cerebral cortex.

A hearing device, e.g. a hearing aid, may be adapted to a particular user's needs, e.g. a hearing impairment. A configurable signal processing circuit of the hearing device may be adapted to apply a frequency and level dependent compressive amplification of an input signal. A customized frequency and level dependent gain (amplification or compression) may be determined in a fitting process by a fitting system based on a user's hearing data, e.g. an audiogram, using a fitting rationale (e.g. adapted to speech). The frequency and level dependent gain may e.g. be embodied in processing parameters, e.g. uploaded to the hearing device via an interface to a programming device (fitting system), and used by a processing algorithm executed by the configurable signal processing circuit of the hearing device.

A 'hearing system' refers to a system comprising one or two hearing devices, and a 'binaural hearing system' refers to a system comprising two hearing devices and being adapted to cooperatively provide audible signals to both of the user's ears. Hearing systems or binaural hearing systems may further comprise one or more 'auxiliary devices', which communicate with the hearing device(s) and affect and/or benefit from the function of the hearing device(s). Auxiliary devices may be e.g. remote controls, audio gateway devices, mobile phones (e.g. smartphones), or music players. Hearing devices, hearing systems or binaural hearing systems may e.g. be used for compensating for a hearing-impaired person's loss of hearing capability, augmenting or protecting a normal-hearing person's hearing capability and/or conveying electronic audio signals to a person. Hearing devices or hearing systems may e.g. form part of or interact with public-address systems, active ear protection systems, handsfree telephone systems, car audio systems, entertainment (e.g. karaoke) systems, teleconferencing systems, classroom amplification systems, etc.

Embodiments of the disclosure may e.g. be useful in applications such as applications.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

The figures are schematic and simplified for clarity, and they just show details which are essential to the understanding of the disclosure, while other details are left out. Throughout, the same reference signs are used for identical or corresponding parts.

Figure 1A:
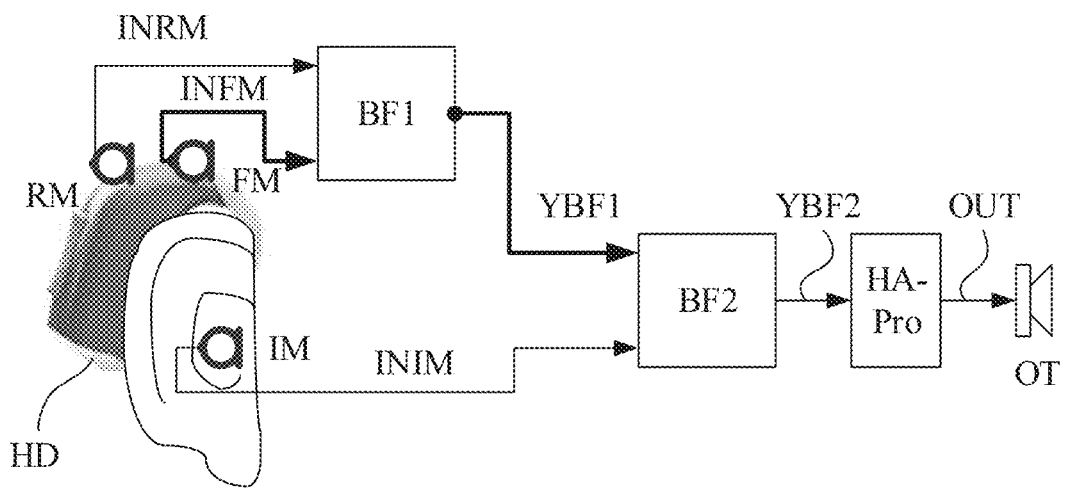
FIG. 1A shows a first embodiment of a hearing system comprising three input transducers and two cascaded two channel beamformers according to the present disclosure.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

The present application relates to the field of hearing devices, e.g. hearing aids.

U.S. Pat. No. 7,471,798 B2 and U.S. Pat. No. 9,301,049 B2 deal with linear microphone arrays, extending a 2-microphone linear array to 3 or more microphones with same microphone distance, assuming a target signal impinging from the front of the user wearing the linear microphone array.

Consider a hearing device utilizing beamforming to enhance the signal to noise ratio (i.e. reducing unwanted background noise) while maintaining the perception of the target (no target loss and unaltered spatial perception).

Beamformers in hearing devices commonly use two microphones. Increasing the number of microphones can increase the degrees of freedom of beamformers in order to improve the enhancement.

Adaptive enhancement algorithms that use multiple microphones typically involve computationally expensive operations such as matrix inverse and eigenvalue decomposition of covariance matrices. The complexity in terms of operations per second will typically increase exponentially as a function of the number of channels.

The main idea of this invention is to combine low complexity 2-channel adaptive beamformer structures in a meaningful way to achieve M-channel adaptive beamforming (where M>2) such as to maximize the beamformer enhancement performance as close to the M-channel full complexity reference as possible.

Two examples of an M=3 microphone configuration are: 1) a configuration with front and rear microphones in a BTE shell and a third microphone situated in the ear. 2) a configuration with a front and rear microphone in a BTE shell and the front microphone in a BTE shell on the contra-lateral ear (binaural configuration).

An example of a M=4 microphone channel configuration is a configuration with a front and rear microphone in a BTE shell, a third microphone situated in the ear and a fourth microphone mounted in a BTE shell on the contra-lateral ear or situated in the contra-lateral ear (binaural configuration).

Figure 5:
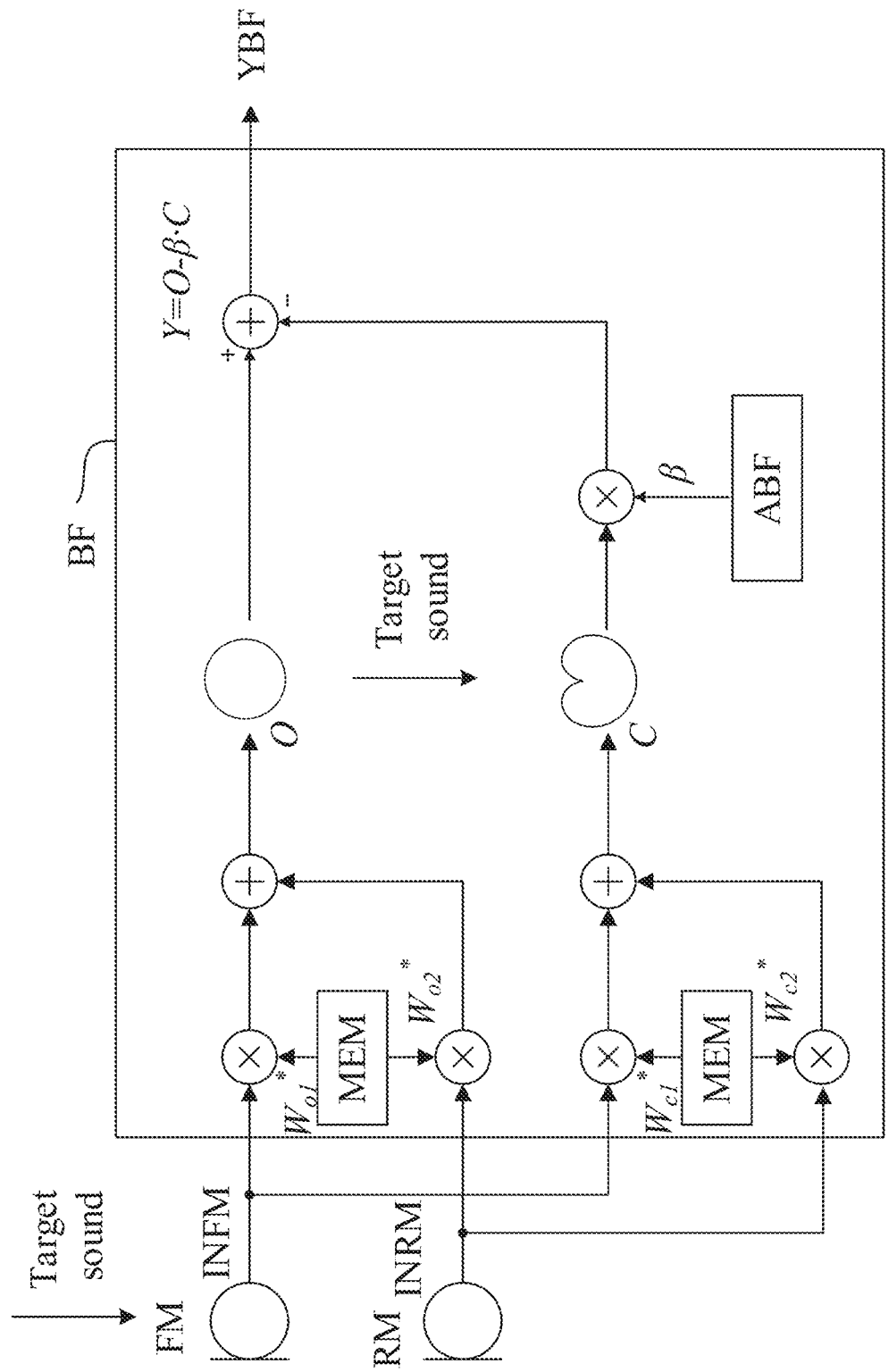
FIG. 5 shows an embodiment of an adaptive two-channel beamformer for providing a beamformed signal based on two (microphone) beamformer-input signals.

An exemplary 2-channel adaptive beamformer building block (cf. 'two-channel beamformers' (BF1, BF2, BF3, BF4, . . . ) in the following drawings) is an adaptive MVDR which aims at reducing the noise as much as possible while maintaining the target. The latter is important in hearing aid context, since target loss with a few dB can have consequences for the audibility of the hearing aid user. The 2-channel beamformer is implemented by applying complex weights in a signal path with complex sub-band analysis/synthesis filter banks. The complex weights are calculated based on a GSC structure. A GSC consists of target-adaptive enhanced omni and target cancelling beamformers and a noise-adaptive scalar β (for a 2-microphone implementation; for M>2, the adaptive parameter β is a vector (of size M−1)). The advantage of such a beamformer is that the behavior of the adaptive beamformer can be controlled in the "beta-space" by simply constraining the value of beta over time, dependent on external parameters such as signal level and SNR. One microphone is defined as a reference microphone (providing a reference input signal), i.e. the beamformer is preserving the target sound as it is present in the reference microphone. Alternatively, a virtual microphone may be defined, and the signal provided by such virtual microphone used as reference input signal. In the latter case, the reference input signal an electric signal determined from the at least three electric input signals as if provided by a (virtual) microphone located at a spatial reference point relative to locations of the at least three input transducers. An example of a two channel beamformer as outlined above is shown in FIG. 5. A 2-channel beamformer may as well be implemented as filters in the time-domain.

The terms 'beamformed signal' and 'spatially filtered signal' are used interchangeably in the present disclosure with no intended difference in meaning.

FIG. 1A shows a first embodiment of a hearing system comprising a hearing device (HD) comprising two cascaded two channel beamformers according to the present disclosure. FIG. 1A illustrates a 3-microphone configuration with a cascade of two 2-channel beamformers. A hearing device (HD) located at an ear of a user comprises three microphones (denoted FM, RM, IM) A BTE part of the hearing device (HD) adapted for being located at the external ear (pinna) of the user comprises two of the three microphones, a front microphone (FM) and a rear microphone (RM), front and rear referring to a wearer's (=user's) normal look direction as 'front' and the opposite direction as 'rear'. An ITE-part of the hearing device (HD) adapted for being located in or at the ear canal of the user comprises a microphone (IM) located in concha, at the ear canal opening, or in the ear canal. The three microphones (FM, RM, IM) each pick up respective 'samples' of the sound field around the user and provide corresponding electric input signals (INFM, INRM, INIM). In the example of FIG. 1A, one of the BTE-microphones (here the front microphone (FM)) is taken to be the reference microphone (as indicated by the bold arrow representing the microphone signal INFM of the front microphone (FM)). The signals (INFM, INRM) from the front and rear microphones (FM, RM) are fed to a two-channel beamformer BF1 providing a (first) beamformed signal (YBF1) as a (possibly complex) linear combination of the (first and second) beamformer-input signals (INFM, INRM). The (first) beamformed signal (YBF1) is fed to a second two-channel beamformer BF2 providing a resulting (second) beamformed signal (YBF2) as a (possibly complex) linear combination of the (third and fourth) beamformer-input signals (YBF1, INIM). The resulting (second) beamformed signal (YBF2) is fed to a processor (HA-Pro) for applying one or more further processing algorithms to the spatially filtered signal (e.g. frequency and level dependent gain/attenuation according to the user's needs, e.g. to compensate for a hearing impairment). The processor provides a processed signal (OUT) that is fed to an output transducer (OT), here a loudspeaker, for providing the processed signal (OUT) as stimuli perceivable by the user as sound (here acoustic stimuli).

The system is configured to maintain a target signal in the signal picked up by the reference microphone. The setup of FIG. 1A will prioritize placing a spatial null in the horizontal plane (wherein the two BTE-microphones (FM, RM) are located). This is reflected in the first beamformed signal YBF1 provided by the primary beamformer (BF1) receiving the reference signal. Residual noise is further reduced by a secondary beamformer (BF2) based on the beamformed signal (YBF1) and the signal (INIM) from the microphone (IM) at or in the ear canal of the user.

Compared to a full three channel beamformer, the present cascade of two-channel beamformers has a computational advantage (the number of computations increases exponentially with M, the number of beamformer inputs (microphones)). A further advantage is that the control of the adaptive parameter of the (M−1) two-channel beamformers (two independent β-values, e.g. β1 and β2 for the first and second two-channel beamformers (BF1, BF2), respectively) is computationally easier than the control of the β-vector for an M-channel beamformer (for M>2).

Figure 1B:
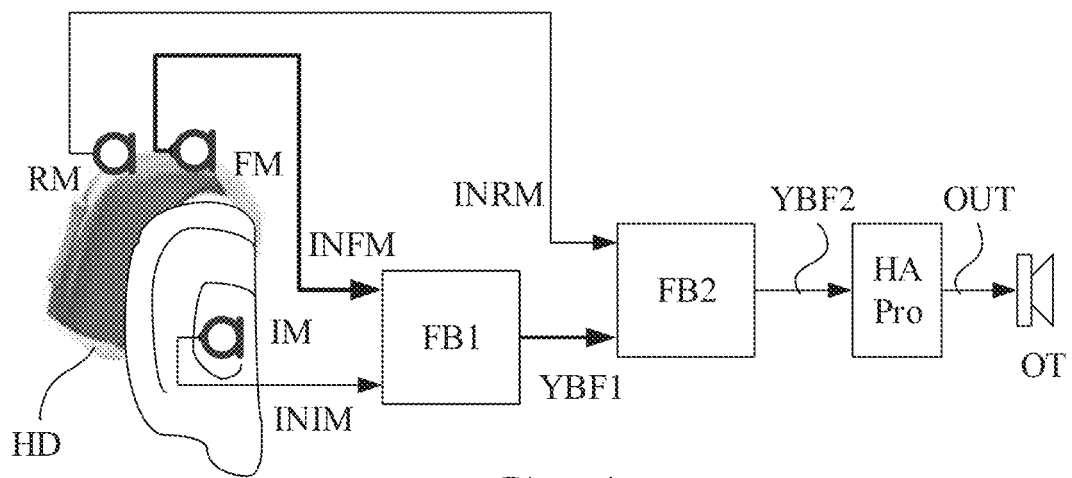
FIG. 1B shows a second embodiment of a hearing system comprising three input transducers and two cascaded two channel beamformers according to the present disclosure.

FIG. 1B shows a second embodiment of a hearing system comprising three input transducers and two cascaded two channel beamformers according to the present disclosure. The embodiment of FIG. 1B is similar to the embodiment of FIG. 1A in that it comprises a hearing device (HD) comprising a 3-microphone configuration (FM, RM, IM) combined in a cascade of 2-channel beamformers (BF1, BF2) to provide a resulting spatially filtered signal (YBF2). The BTE-front microphone (FM) is the reference microphone (as in FIG. 1A). As a difference to the embodiment of FIG. 1A, the ITE-front microphone (IM) is fed to the primary (first) two channel beamformer (BF1) together with the reference signal (INFM) from the front microphone (FM) providing the first beamformed signal (YBF1). The secondary (second) two-channel beamformer (BF2) receives as inputs the first beamformed signal (YBF1) and the rear microphone signal (INRM) and provides the resulting beamformed signal (YBF1), which is fed to the processor (HA-Pro) for further processing, etc. (as in FIG. 1A).

This setup will prioritize placing a spatial null in the vertical plane and residual noise is further reduced by the secondary beamformer (BF2). The configuration in FIG. 1A is preferred over the configuration in FIG. 1B, since (it is assumed that) the target sound will primarily be impinging from the front direction (0 deg. azimuth), and experiments have shown that this configuration approximates a 3-channel adaptive MVDR beamformer very well (MVDR=minimum variance distortionless response).

Figure 1C:
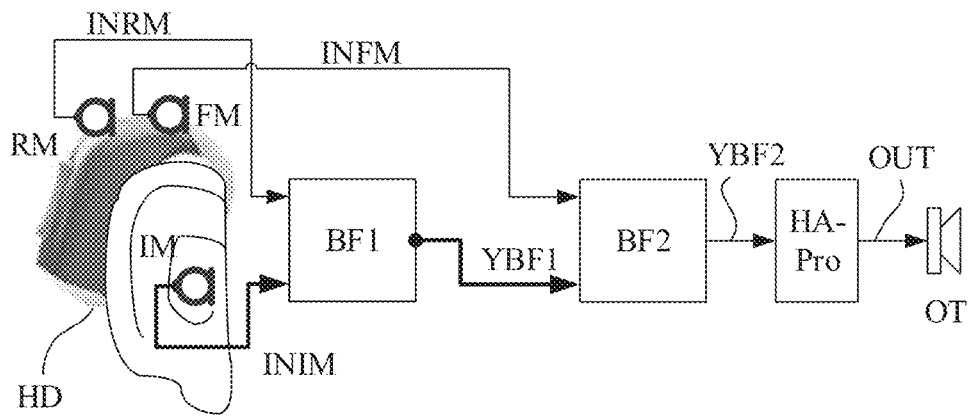
FIG. 1C shows a third embodiment of a hearing system comprising three input transducers and two cascaded two channel beamformers according to the present disclosure.

FIG. 1C shows a third embodiment of a hearing system comprising three input transducers and two cascaded two channel beamformers according to the present disclosure. The embodiment of FIG. 1C is similar to the embodiment of FIG. 1A in that it comprises a hearing device (HD) comprising a 3-microphone configuration (FM, RM, IM) combined in a cascade of 2-channel beamformers (BF1, BF2) to provide a resulting spatially filtered signal (YBF2). As a difference to the embodiment of FIG. 1A, the ITE-front microphone (IM) is the reference microphone in the embodiment of FIG. 1C. In the embodiment of FIG. 1C, the reference microphone signal (INIM) and the rear microphone signal (INRM) are fed to the first two-channel beamformer (BF1) providing the first beamformed signal (YBF1). The first beamformed signal (YBF1), together with the front microphone signal (INFM) are fed to the second two-channel beamformer (BF2) providing the resulting (second) beamformed signal (YBF2), which is fed to the hearing device processor HA-Pro for further processing, etc. (as discussed in connection with FIG. 1A).

The benefit of this configuration is the preservation of pinna cues. The coupling of the signal (INFM) from the front microphone (FM) and the signal (INRM) from the rear microphone (RM) to the first and second beamformers (BF1, BF2) can be interchanged.

Figure 1D:
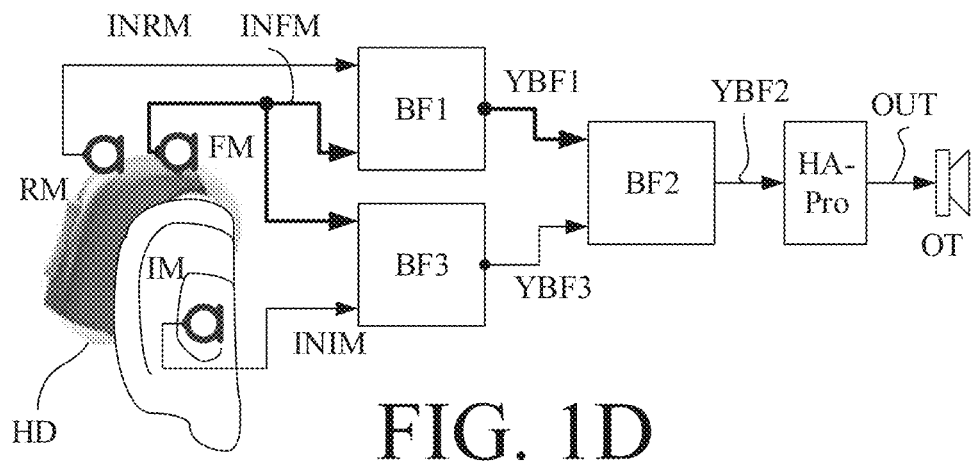
FIG. 1D shows a first embodiment of a hearing system comprising three input transducers and three channel beamformers according to the present disclosure.

FIG. 1D shows a first embodiment of a hearing system comprising three input transducers and three channel beamformers according to the present disclosure. FIG. 1D illustrates a further example of a 3-microphone configuration of a hearing system, e.g. a hearing device. The hearing system comprises a tree-structure of three 2-channel beamformers (BF1, BF2, BF3). The BTE-front microphone (FM) is the reference microphone. As a difference to the embodiment of FIG. 1A, the embodiment of FIG. 1D comprises an additional (primary) two-channel beamformer (BF3), which receives the reference microphone signal INFM (from front microphone FM) and the electric input signal (INIM) from the ITE-microphone (IM). The additional two-channel beamformer (BF3) provides spatially filtered signal YBF3 as a (possibly complex) linear combination of the beamformer-input signals (INFM, INIM). Instead of the electric input signal (INIM) from the ITE-microphone (IM), the second two channel beamformer (BF2) of FIG. 1D receives the third spatially filtered signal (YBF3) as beamformer input together with the first beamformed signal (YBF1) to thereby provide the resulting beamformed signal (YBF2).

At the cost of somewhat increased computational complexity, the two primary beamformers (BF1, BF3) will reduce noise individually and the secondary beamformer (BF2) will attenuate any residual noise further. Both primary beamformer outputs (YBF1 and YBF3, respectively) could be the reference of the secondary beamformer (BF2). A similar configuration could be made, where the microphone in the ear (IM) is the reference.

Figure 1E:
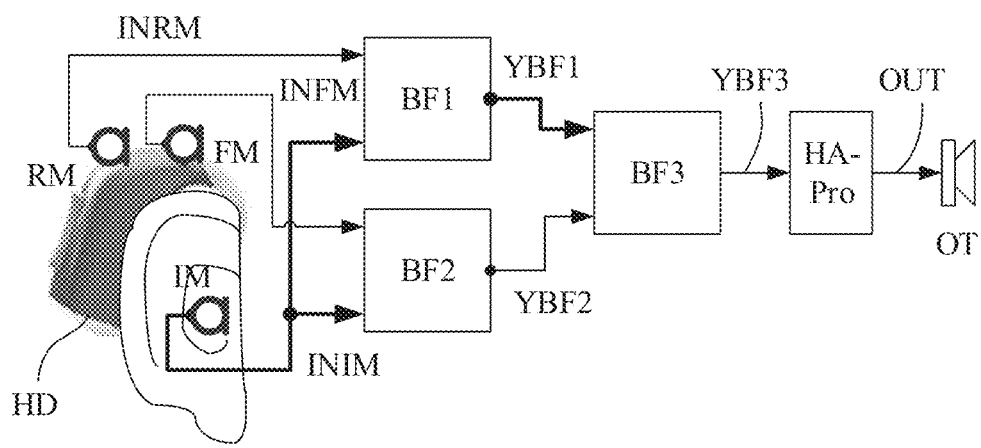
FIG. 1E shows a second embodiment of a hearing system comprising three input transducers and three channel beamformers according to the present disclosure.

FIG. 1E shows a second embodiment of a hearing system comprising three input transducers and three channel beamformers according to the present disclosure. The embodiment of FIG. 1E is similar to the embodiment of FIG. 1D. The difference is that the electric input signal INIM from the ITE-microphone (IM) is the reference signal (instead of the electric input signal INFM from the front-microphone (FM) of the BTE-part of the hearing device in FIG. 1D). This has the advantage of including the spatial cues of pinna in the first (and second) beamformed signal(s) (YBF1, YBF2).

Figure 2A:
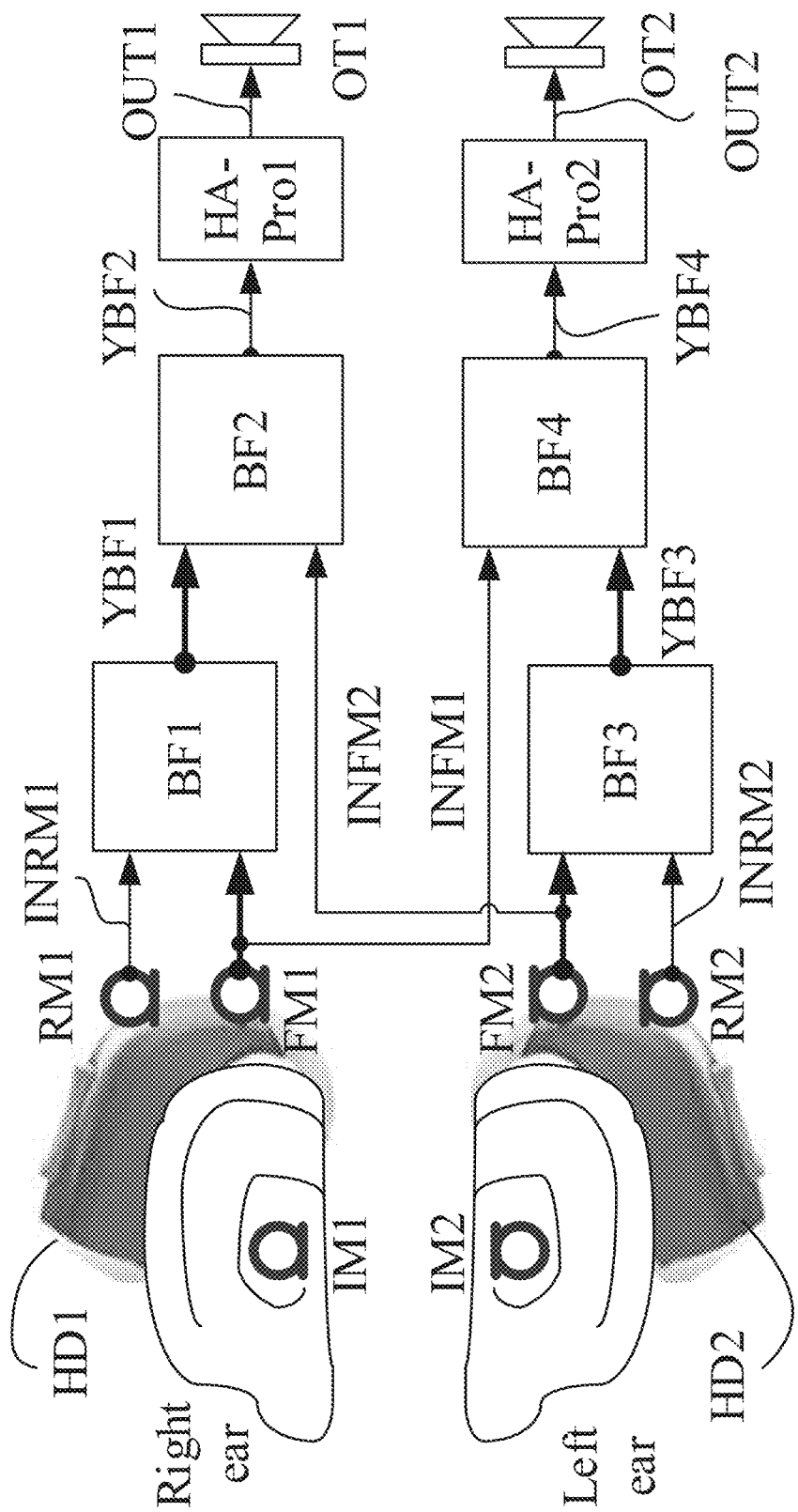
FIG. 2A shows a first embodiment of a hearing system comprising first and second hearing devices according to the present disclosure.

FIG. 2A shows an embodiment of a hearing system comprising first and second hearing devices (HD1, HD2) according to the present disclosure. The first and second hearing devices are adapted for being located at the right and left ears, respectively, of a user. A 3-microphone binaural configuration is illustrated with a cascade of two 2-channel beamformers in each hearing device. The configuration of each of the first and second hearing devices (HD1, HD2) are similar to the embodiment of a hearing device shown in and discussed in connection with FIG. 1A. The front microphone (FN1, FM2) of the first and second hearing devices (HD1, HD2), respectively, is the reference microphone (as in FIG. 1A). The secondary beamformer (BF2, BF4), respectively, is a binaural beamformer, attenuating the residual noise and providing respective resulting beamformed signals YBF2, YBF4 that are fed to respective hearing aid processors (HA-Pro1, HA-Pro2) whose respective outputs are fed to respective output transducers (OT1, OT2) as discussed in connection with FIG. 1. The respective binaural beamformers (BF2, BF4) receive a signal (INFM1, INFM2) from the front microphone (FM1, FM2) of the respective opposite hearing device (as opposed to the signal INIM from the ITE-microphone as shown in FIG. 1A). This will be preferred when the target is in the front. When the target is impinging from the side (90 or 270 degrees azimuth), it is preferred to apply the binaural beamformer first and use the rear microphone in the secondary beamformer.

Figure 2B:
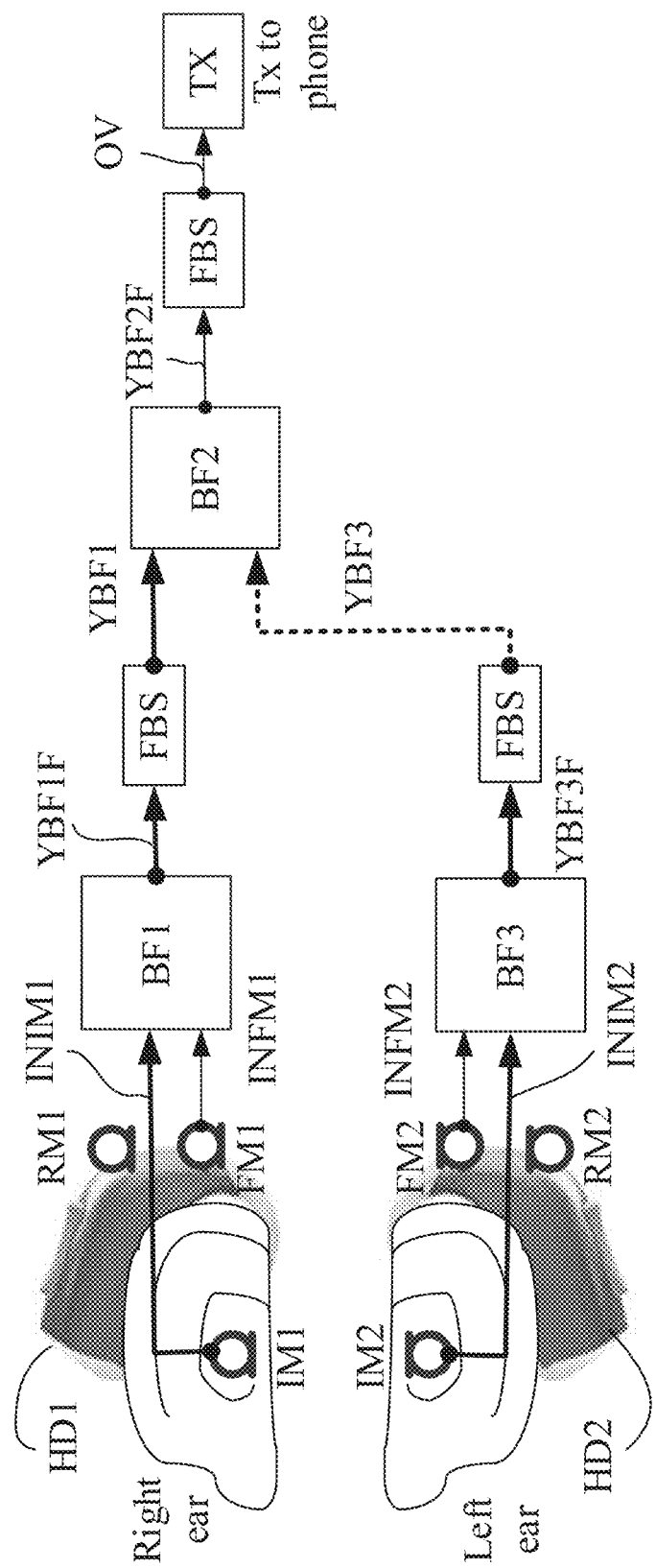
FIG. 2B shows a second embodiment of a hearing system comprising first and second hearing devices according to the present disclosure, specifically suitable for pick up of a user's own voice.

FIG. 2B shows a second embodiment of a hearing system comprising first and second hearing devices according to the present disclosure, specifically suitable for pick up of a user's own voice. The hearing system of FIG. 2B uses as inputs to the respective primary 2-channel beamformers BF1 and BF3 (of the first and second hearing devices, respectively) the ITE-microphone signals (INIM1 and INIM2) as reference signals and provides the respective front microphone signals INFM1 and INFM2 (of the BTE-parts) as the second beamformer-input signals. It is assumed that the primary 2-channel beamformers BF1 and BF2 work in the frequency (sub-band) domain and each provides respective beamformed signals YBF1F and YBF3F also in the frequency domain. For simplicity, the beamformed signals YBF1F and YBF3F are transformed to time domain signals YBF1 and YBF3 in respective synthesis filter banks (FBS). In the exemplary embodiment of FIG. 2B, the further processing to provide the own voice signal is performed in the first hearing device (HD1). Hence the time domain beamformed signal YBF3 from primary 2-channel beamformers BF3 of the second hearing device (HD2) is fed to antenna and transceiver circuitry (not shown) and transmitted to and received by appropriate antenna and transceiver circuitry (not shown) in the first hearing device (HD1), as indicated by dotted arrow YBF3. The two beamformed (time domain) signals YBF1 and YBF3 are fed to a two-channel frequency-domain beamformer (BF2) (including conversion from time- to frequency-domain signals) providing beamformed signal YBF2F comprising an estimate of the users own voice in the frequency domain. The beamformed signal YBF2F is fed to a synthesis filter bank (FBS) and the resulting estimate of the user's own voice (OV) in the time-domain is fed to transceiver TX and transmitted to another device, e.g. to a communications device, e.g. a telephone. An advantage of using the combination of a BTE-microphone and an ITE-microphone as the two beamformer-input signals to the respective primary beamformers (BF1, BF2) of the first and second hearing devices (HD1, HD2) is that the respective microphone axes point downwards (or upwards), e.g. towards the mouth of the user. Hence such beamformers are suitable for maintaining a signal originating from the user's mouth (or more generally in directions perpendicular to a horizontal plane). Target directions in the horizontal plane are e.g. served by a microphone configuration using the two BTE-microphones as inputs to the primary 2-channel beamformer(s).

Figure 3:
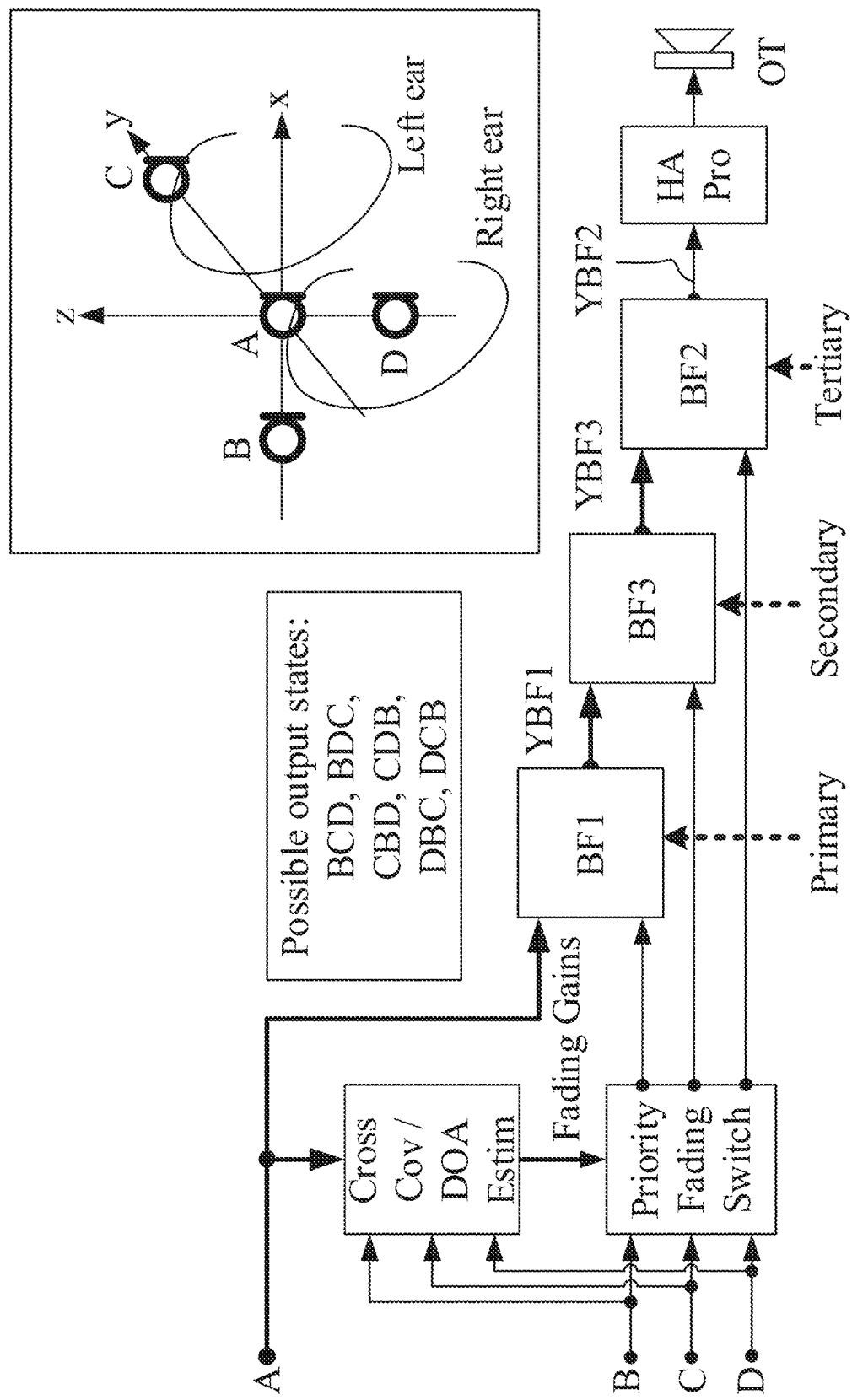
FIG. 3 shows an embodiment of a hearing system comprising four microphones according to the present disclosure.

FIG. 3 shows an embodiment of a hearing system comprising four microphones (A, B, C, D) according to the present disclosure. The 4-microphone configuration provides options for several meaningful combinations of microphone order, and beamformer cascading structures, which can effectively approximate the performance of a full 4-microphone beamformer. Consider microphone placements in the xyz orthogonal coordinate system of the top right part of FIG. 3, where A=Front, B=Rear, C=Contralateral Front and D=In the Ear. In this example, the front microphone (A) is the reference microphone (placed in (0, 0, 0)). Dependent on the target direction, one of the microphones B (target in x-direction), C (target in y-direction) or D (target in z-direction) is the secondary input of the primary, secondary (BF3) and tertiary (BF2) beamformer (cf. indication by bold, dashed arrows in the lower part of FIG. 3 of the different categories, 'primary', 'secondary', 'tertiary', . . . , of the layered structure of 2-channel beamformers indicated). A fading algorithm (Cross/Cov DOA Estim-unit) can adaptively control which of the microphones B, C or D is the secondary input of the primary (BF1), secondary (BF3) or tertiary (BF2) beamformer. Fading can be controlled based on the covariance C(AB,target), C(AC,target) and C(AD, target) and/or derivatives thereof, for example DOA estimates. The fading algorithm (Cross/Cov DOA Estim-unit) receives all four microphone signals (A, B, C, D) and based thereon determines a target direction (e.g. a target sound source comprising speech). The resulting control signal (Fading gains) is fed to a switching unit (Priority Fading Switch) which—based on the determined location of or direction to the target sound source—sets respective switches to route electric input signals (B, C, D) to the appropriate ones of the two-channel beamformers (BF1, BF2, BF3).

In another embodiment, only one (primary) two-channel beamformer is active at a given point in time (e.g. in a specific mode of operation; e.g. to same power). In this mode, the second beamformer-input signal (in addition to the reference input signal) to the primary two-channel beamformer (BF1) is adaptively selected by the fading algorithm (Cross/Cov DOA Estim-unit) the switching unit (Priority Fading Switch). In this embodiment, the resulting beamformed signal (e.g. YBF1) is then fed directly to the processor HA-Pro for further hearing aid processing.

Figure 4:
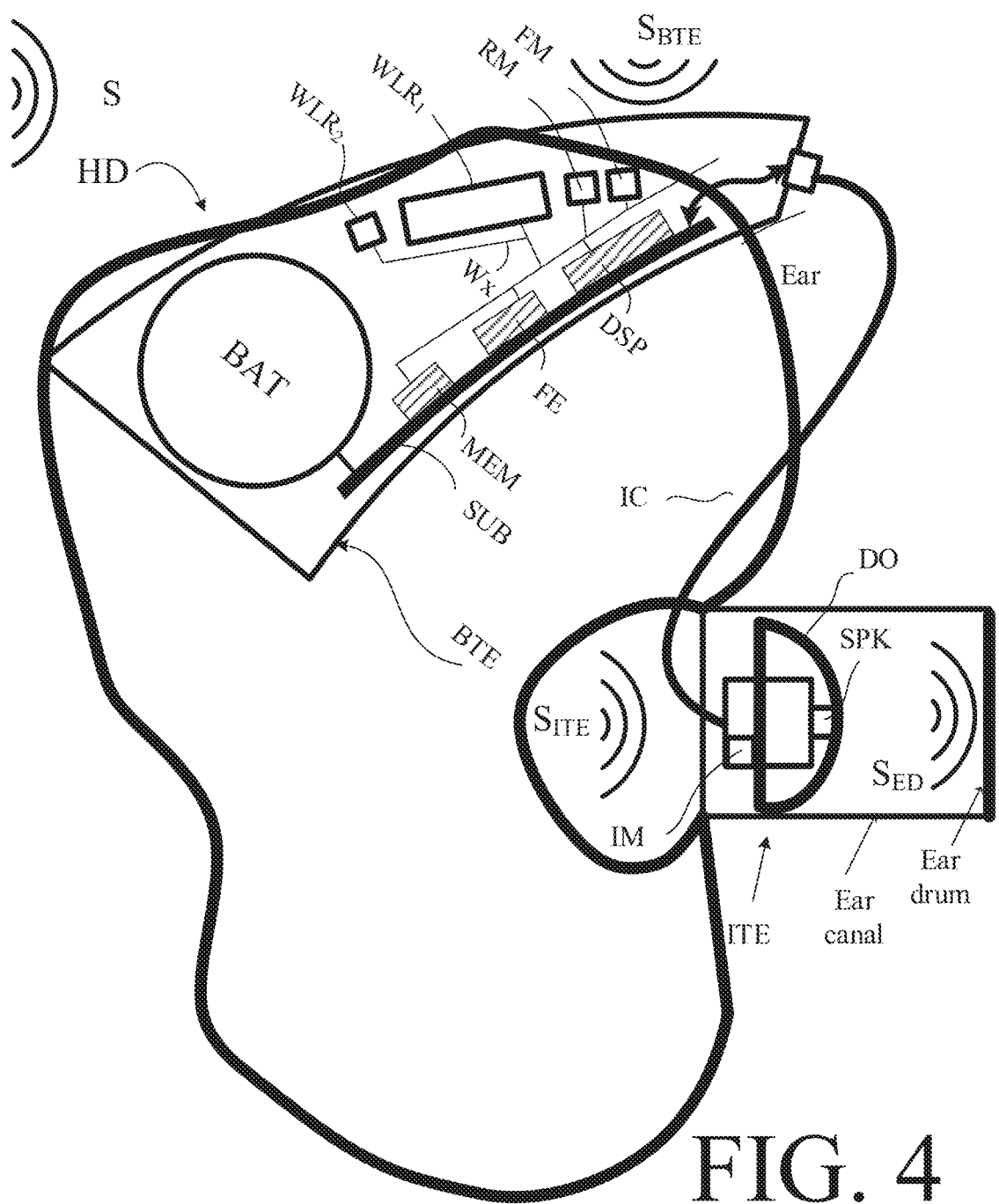
FIG. 4 shows an embodiment of a hearing device according to the present disclosure.

FIG. 4 shows an embodiment of a hearing device according to the present disclosure. The hearing device (HD), e.g. a hearing aid, is of a particular style (sometimes termed receiver-in-the ear, or RITE, style) comprising a BTE-part (BTE) adapted for being located at or behind an ear of a user, and an ITE-part (ITE) adapted for being located in or at an ear canal of the user's ear and comprising a receiver (loudspeaker). The BTE-part and the ITE-part are connected (e.g. electrically connected) by a connecting element (IC) and internal wiring in the ITE- and BTE-parts (cf. e.g. wiring Wx in the BTE-part). The connecting element may alternatively be fully or partially constituted by a wireless link between the BTE- and ITE-parts.

In the embodiment of a hearing device in FIG. 4, the BTE part comprises two input units comprising respective input transducers (e.g. microphones) (FM, RM), each for providing an electric input audio signal representative of an input sound signal (SBTE) (originating from a sound field S around the hearing device). The input unit further comprises two wireless receivers ($WLR_1$, $WLR_2$) (or transceivers) for providing respective directly received auxiliary audio and/or control input signals (and/or allowing transmission of audio and/or control signals to other devices, e.g. a remote control or processing device). The hearing device (HD) comprises a substrate (SUB) whereon a number of electronic components are mounted, including a memory (MEM) e.g. storing different hearing aid programs (e.g. parameter settings defining such programs, or parameters of algorithms, e.g. optimized parameters of a neural network) and/or hearing aid configurations, e.g. input source combinations (FM, RM, IM, $WLR_1$, $WLR_2$), e.g. optimized for a number of different listening situations. In a specific mode of operation, one or more directly received auxiliary electric signals are used together with one or more of the electric input signals from the microphones to provide a beamformed signal provided by applying appropriate complex weights to the respective signals.

The substrate further comprises a configurable signal processor (DSP, e.g. a digital signal processor, e.g. including a processor for applying a frequency and level dependent gain, e.g. providing beamforming, noise reduction, filter bank functionality, and other digital functionality of a hearing device according to the present disclosure). The configurable signal processor (DSP) is adapted to access the memory (MEM) and for selecting and processing one or more of the electric input audio signals and/or one or more of the directly received auxiliary audio input signals, based on a currently selected (activated) hearing aid program/parameter setting (e.g. either automatically selected, e.g. based on one or more sensors, or selected based on inputs from a user interface). The mentioned functional units (as well as other components) may be partitioned in circuits and components according to the application in question (e.g. with a view to size, power consumption, analogue vs. digital processing, etc.), e.g. integrated in one or more integrated circuits, or as a combination of one or more integrated circuits and one or more separate electronic components (e.g. inductor, capacitor, etc.). The configurable signal processor (DSP) provides a processed audio signal, which is intended to be presented to a user. The substrate further comprises a front-end IC (FE) for interfacing the configurable signal processor (DSP) to the input and output transducers, etc., and typically comprising interfaces between analogue and digital signals. The input and output transducers may be individual separate components, or integrated (e.g. MEMS-based) with other electronic circuitry.

The hearing device (HD) further comprises an output unit (e.g. an output transducer) providing stimuli perceivable by the user as sound based on a processed audio signal from the processor or a signal derived therefrom. In the embodiment of a hearing device in FIG. 4, the ITE part comprises the output unit in the form of a loudspeaker (also termed a 'receiver') (SPK) for converting an electric signal to an acoustic (air borne) signal, which (when the hearing device is mounted at an ear of the user) is directed towards the ear drum (Ear drum), where sound signal (SED) is provided. The ITE-part further comprises a guiding element, e.g. a dome, (DO) for guiding and positioning the ITE-part in the ear canal (Ear canal) of the user. The ITE-part further comprises a further input transducer, e.g. a microphone (IM), for providing an electric input audio signal representative of an input sound signal (SITE) at the ear canal.

The electric input signals (from input transducers FM, RM, IM) may be processed in the time domain or in the (time-) frequency domain (or partly in the time domain and partly in the frequency domain as considered advantageous for the application in question) using one or more two-channel beamformers as proposed in the present disclosure.

The hearing device (HD) exemplified in FIG. 4 is a portable device and further comprises a battery (BAT), e.g. a rechargeable battery, e.g. based on Li-Ion battery technology, e.g. for energizing electronic components of the BTE- and possibly ITE-parts. In an embodiment, the hearing device, e.g. a hearing aid, is adapted to provide a frequency dependent gain and/or a level dependent compression and/or a transposition (with or without frequency compression) of one or more frequency ranges to one or more other frequency ranges, e.g. to compensate for a hearing impairment of a user. The BTE-part may e.g. comprise a connector (e.g. a DAI or USB connector) for connecting a 'shoe' with added functionality (e.g. an FM-shoe or an extra battery, etc.), or a programming device, or a charger, etc., to the hearing device (HD).

FIG. 5 shows an embodiment of an adaptive two-channel beamformer for providing a beamformed signal based on two (microphone) beamformer-input signals. FIG. 1 shows a part of a hearing aid comprising first and second microphones (M1, M1) providing respective first and second electric input signals INM1 and INM2, respectively, and a two-channel beamformer (BF) providing a beamformed signal YBF based on the first and second electric input signals (INM1, INM2). A direction from the target signal to the hearing aid is e.g. defined by the microphone axis and indicated in FIG. 5 by arrow denoted Target sound. The target direction can be any direction, e.g. a direction to the user's mouth (to pick up the user's own voice), or other directions to target signal source (e.g. to the side of or above the user). An adaptive beam pattern (Y (Y(k))), for a given frequency band k, k being a frequency band index, may be obtained by linearly combining an omnidirectional delay-and-sum-beamformer (O (O(k))) and a delay-and-subtract-beamformer (C (C(k))) in that frequency band. The omnidirectional signal from the delay-and-sum-beamformer (O (O(k))) is provided as linear combination of the beamformer-input signals INM1*Wo1+INM2*Wo2. The signal from the delay-and-subtract-beamformer (C (C(k))) is provided as a linear combination of the beamformer-input signals INM1*Wc1+INM2*Wc2. The weights Wo1, Wo2, Wc1, Wc2 are complex frequency dependent constants, e.g. stored in a memory (MEM) of the hearing device. The adaptive beam pattern arises by scaling the delay-and-subtract-beamformer (C(k)) by a complex-valued, frequency-dependent, adaptive scaling factor β(k) (generated by beamformer ABF) before subtracting it from the delay-and-sum-beamformer (O(k)), i.e. providing the beam pattern Y, $$Y(k)=O(k)-\beta(k)C(k).$$

It should be noted that the sign in front of β(k) might as well be +, if the sign(s) of the weights constituting the delay-and-subtract beamformer C is appropriately adapted. Further, β(k) may be substituted by β*(k), where * denotes complex conjugate, such that the beamformed signal $Y_{BF}$ is expressed as $Y_{BF}=(w_o(k)-\beta(k)\cdot w_c(k))^H \cdot IN(k)$.

The two-channel beamformer (BF) is e.g. adapted to work optimally in situations where the microphone signals consist of a localized target sound source in the presence of additive noise sources. Given this situation, the scaling factor β(k) (β in FIG. 5) is adapted to minimize the noise under the constraint that the sound impinging from the target direction (at least at one frequency) is essentially unchanged. For each frequency band k, the adaptation factor β(k) can be found in different ways. The solution may be found in closed form as $$\beta(k) = \frac{\langle C^* O \rangle}{\langle |C|^2 \rangle},$$

where * denote the complex conjugation and ⟨·⟩ denotes the statistical expectation operator, which may be approximated in an implementation as a time average. The expectation operator ⟨·⟩ may be implemented using e.g. a first order IIR filter, possibly with different attack and release time constants. Alternatively, the expectation operator may be implemented using an FIR filter. The adaptive 2-channel beamformer may e.g. be a Minimum Variance Distortionless Response (MVDR) type beamformer, as e.g. described in [*Brandstein & Ward;* 2001] (Chapter 2.3 Eq. 2.25).

In a further embodiment, the adaptive 2-channel beamformer is configured to determine the adaptation parameter $\beta_{opt}(k)$ from the following expression $$\beta_{opt} = \frac{w_O^H C_v w_C}{w_C^H C_v w_C},$$

where $w_O$ and $w_C$ are the beamformer weights for the delay and sum O and the delay and subtract C beamformers, respectively, C is the noise covariance matrix, and H denotes Hermitian transposition. Such beamformer has a generalized sidelobe canceller structure, GSC.

For comparison, in an M>2 GSC beamformer, the β-parameter is an (M−1)×1 size vector, defined by $$\beta_{opt} = (W_C^H C_v W_C)^{-1} W_C^H C_v W_O,$$

where $W_C^H$ is known as a size (M−1)×M blocking matrix and $W_O$ is an M×1 beamformer vector. The main influence on the complexity is the (M−1) size matrix inverse operation, which is more expensive than M−1 divisions.

Figure 6:
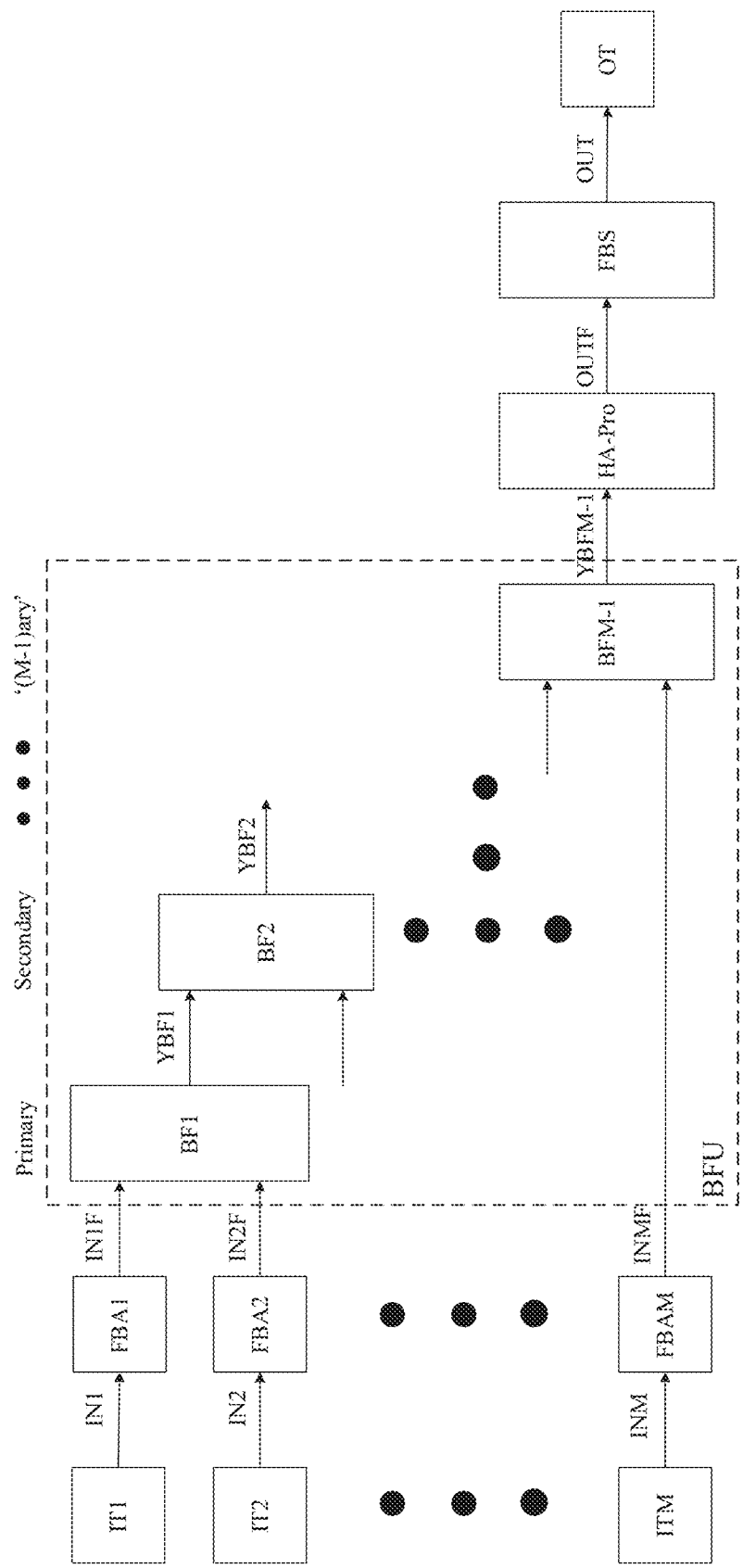
FIG. 6 shows an embodiment of an M-input hearing system comprising M−1 cascaded two-channel beamformers, each M−1-input transducer being coupled to an analysis filter bank to provide the electric input signal as a number of frequency sub-band signals.

FIG. 6 shows an embodiment of an M-input hearing system comprising M−1 cascaded two-channel beamformers, each M−1-input transducer being coupled to an analysis filter bank to provide the electric input signal as a number of frequency sub-band signals. The hearing system of FIG. 6 comprises a multitude M>2 input transducers each being coupled to respective analysis filter banks (FBA1, FBA2, ..., FBAM) to provide the electric input signals (IN1, IN2, ..., INM) from the input transducers (e.g. microphones) in a frequency sub-band (time-frequency) representation (IN1F, IN2F, ..., INMF), which are fed to a beamformer filtering unit (BFU) comprising a layered structure of cascaded 2-channel beamformers (BF1, BF2, ..., BFM−1, here in a pruned structure; could be any other structure, e.g. a tree-like structure) according to the present disclosure (cf. 'primary, 'secondary' and '(M−1)ary' indication of the individual layers in the top part of FIG. 6). The beamformer filtering unit (BFU) provides a beamformed signal (YBFM−1) comprising a reference input signal, which is fed to a processor of the system (HA-Pro) for further processing. The processor provides a processed output signal (OUTF), which is fed to a synthesis filter bank (FBS) for conversion to a time domain signal (OUT). The time domain output signal (OUT) is fed to an output transducer (OT) for providing stimuli perceivable as sound to the user of the hearing system.

Figure 7A:
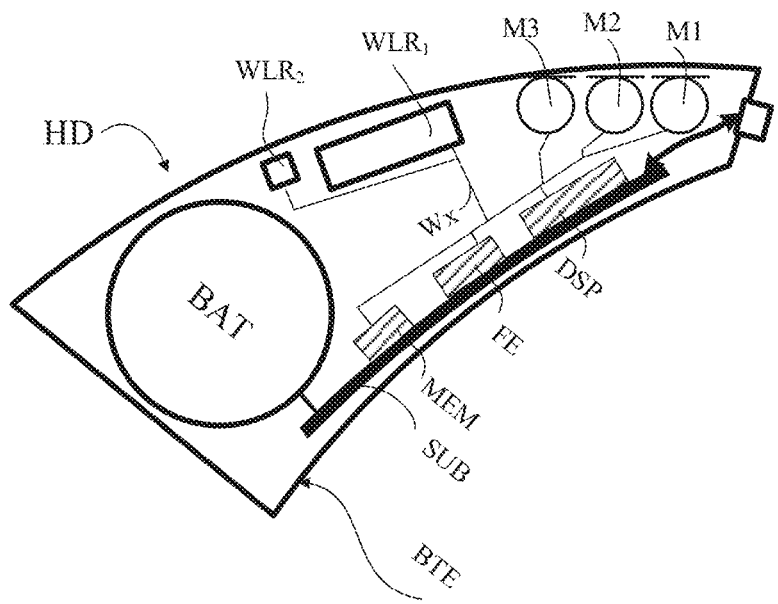
FIG. 7A shows a first exemplary location of three microphones in a BTE-part of a hearing device according to the present disclosure.
Figure 7B:
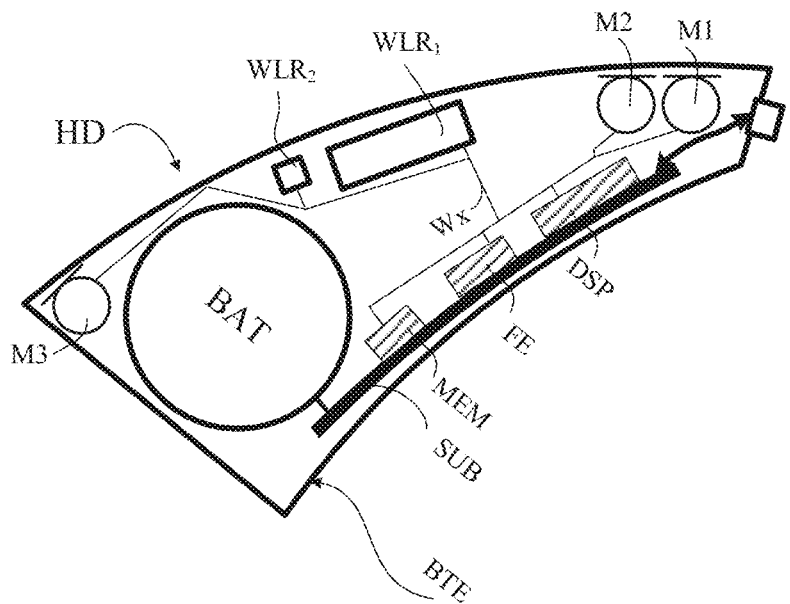
FIG. 7B shows a second exemplary location of three microphones in a BTE-part of a hearing device according to the present disclosure.

FIGS. 7A and 7B shows first and second exemplary location of three microphones (M1, M2, M3) in a BTE-part (BTE) of a hearing device (HD) according to the present disclosure. The embodiments of FIGS. 7A and 7B both resemble the BTE-part (BTE) of the embodiment of a hearing device shown in and discussed in connection with FIG. 4. The embodiments of FIGS. 7A and 7B illustrate respective two different microphone configurations. In FIG. 7A, the three microphones (M1, M2, M3) of the BTE-part are located on a straight line, as linear array (with uniform microphone distance) in the top part of the housing of the BTE-part. The microphone location is intended to provide that the microphone axis points in a look direction of the user, when the user wears the hearing device (HD) at the ear (i.e. when the BTE-part is located at or behind the external ear so that the microphone axis is located in a horizontal plane). In FIG. 7B, only two (M1, M2) of the three microphones of the BTE-part are located in the top part of the housing of the BTE-part, whereas the third microphone (M3) is located in the 'bottom of the housing of the BTE-part, close to the battery. The 'off-axis-location' of the third microphone (M3) creates improved options for maintaining target signals from directions above or below a horizontal plane defined by the upper part of the external ears of the user (where the other microphones (M1, M2) are located. Other microphone placements and more microphones are possible and may be chosen according to the application in question with a view to expected locations of sound sources relative to the user.

Figure 8A:
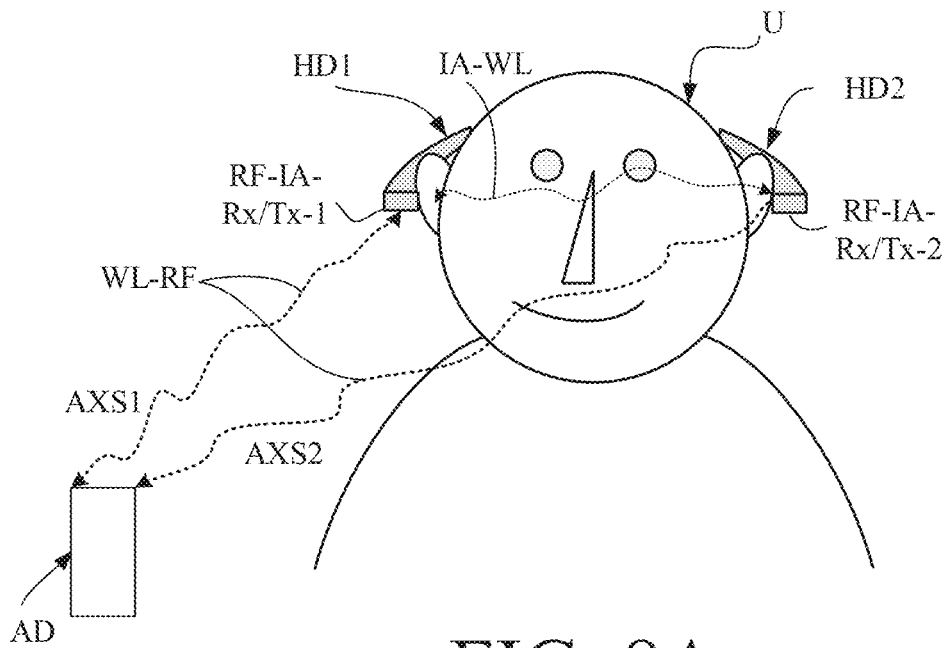
FIG. 8A illustrates an embodiment of a hearing system, e.g. a binaural hearing aid system, according to the present disclosure.

FIG. 8A illustrates an embodiment of a hearing system, e.g. a binaural hearing aid system, according to the present disclosure. The hearing system comprises left and right hearing devices in communication with an auxiliary device, e.g. a remote control device, e.g. a communication device, such as a cellular telephone or similar device capable of establishing a communication link to one or both of the left and right hearing devices.

Figure 8B:
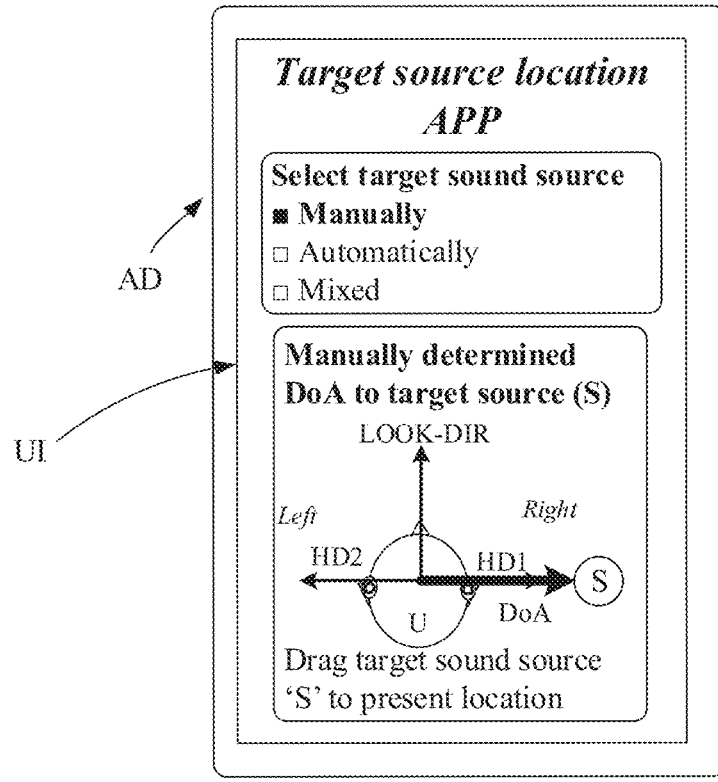
FIG. 8B illustrates an auxiliary device configured to execute an APP for selecting a mode of operation of the hearing system where a location of or a direction to a target sound source of current interest to the user can be shown and/or indicated.

FIG. 8A, 8B together illustrate an application scenario comprising an embodiment of a binaural hearing aid system comprising first (right) and second (left) hearing devices (HD1, HD2) and an auxiliary device (AD) according to the present disclosure. The auxiliary device (AD) comprises a cellular telephone, e.g. a SmartPhone. In the embodiment of FIG. 8A, the hearing devices and the auxiliary device are configured to establish wireless links (WL-RF) between them, e.g. in the form of digital transmission links according to the Bluetooth standard (e.g. Bluetooth Low Energy, or equivalent technology). The links may alternatively be implemented in any other convenient wireless and/or wired manner, and according to any appropriate modulation type or transmission standard, possibly different for different audio sources. The auxiliary device (e.g. a SmartPhone) of FIG. 8A, 8B comprises a user interface (UI) providing the function of a remote control of the hearing aid system, e.g. for changing program or operating parameters (e.g. volume) in the hearing device(s), etc. The user interface (UI) of FIG. 8B illustrates an APP (denoted 'target source location APP') for selecting a mode of operation of the hearing system where a location of or a direction to a target sound source relative to the user (the left and right hearing devices (HD2, HD1) is or can be indicated. The APP allows a user to select a manual (Manually), and automatic (Automatically) or a mixed (Mixed) mode.

In the screen of FIG. 8B, the manual mode of operation has been selected as indicated by the left solid 'tick-box' and the bold face indication 'Manually'. In this mode, the direction of arrival of a target sound source is indicated manually by dragging a symbol 'S' to the current location. Alternatively, the location or direction may be automatically determined (as described in the present disclosure). The resulting location or direction is displayed in the screen by circular symbol denoted S and bold arrow denoted DoA schematically shown relative to the head of the user to reflect its estimated location (here exemplified 'to the right' of the user). This is indicated by the text 'Manually determined DoA to target source (S)' in the lower part of the screen in FIG. 8B. In a mixed mode (Mixed), the user may indicate a rough direction to the target sound source (e.g. the quarter plane wherein the target sound source is located), and then the specific direction of arrival is determined according to the present disclosure (whereby the calculations are simplified by excluding a part of the possible space).

In an embodiment, the calculations of the sound source location encoding parameter, e.g. a direction of arrival, are performed in the auxiliary device. In another embodiment, the calculations are performed in the left and/or right hearing devices. In the latter case the system is configured to exchange the data defining location or the direction of arrival of the target sound signal between the auxiliary device and the hearing device(s). The hearing device (HD1, HD2) are shown in FIG. 8A as devices mounted at the ear (behind the ear) of a user (U). Other styles may be used, e.g. located completely in the ear (e.g. in the ear canal), fully or partly implanted in the head, etc. Each of the hearing instruments comprise a wireless transceiver to establish an interaural wireless link (IA-WL) between the hearing devices, e.g. based on inductive communication or RF communication (e.g. Bluetooth technology). Each of the hearing devices further comprises a transceiver for establishing a wireless link (WL-RF, e.g. based on radiated fields (RF)) to the auxiliary device (AD), at least for receiving and/or transmitting signals (AXS1, AXS2), e.g. control signals, e.g. information signals (e.g. DoA), e.g. including audio signals. The transceivers are indicated by RF-IA-Rx/Tx-1 and RF-IA-Rx/Tx-2 in the right (HD1) and left (HD2) hearing devices, respectively.

Figure 9:
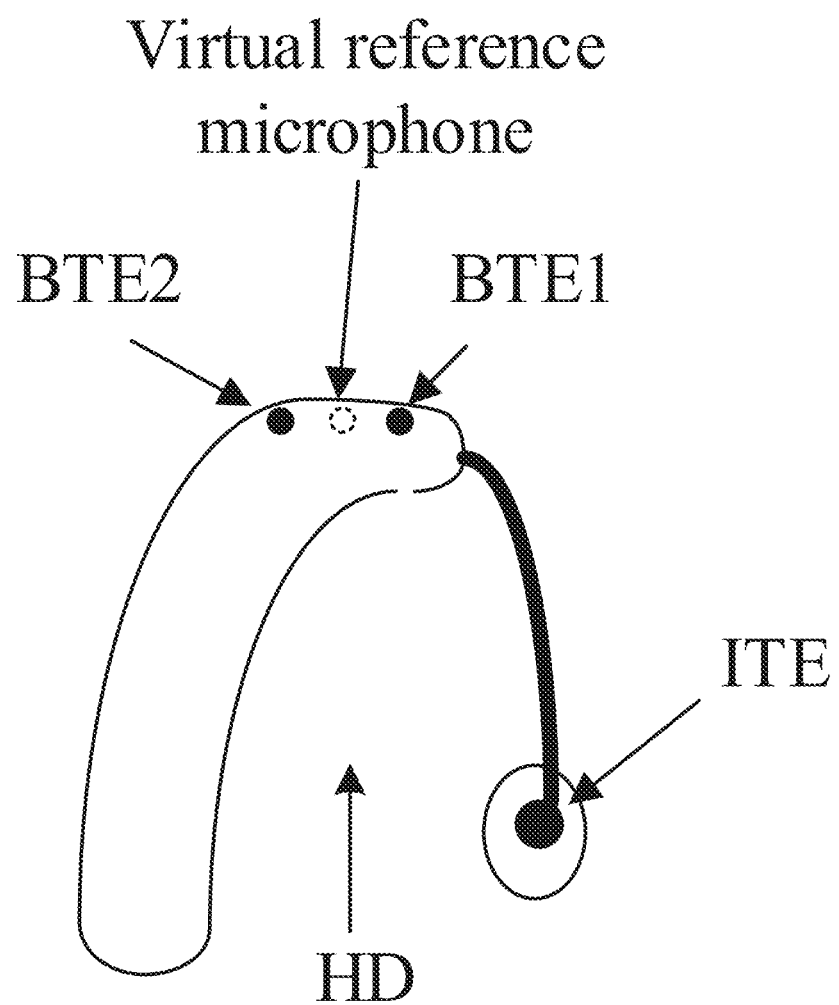
FIG. 9 illustrates the location of a virtual reference microphone in a hearing device according to the present disclosure.

FIG. 9 illustrates a n exemplary location of a virtual reference microphone (Virtual reference microphone) in a hearing device (HD) according to the present disclosure. The location, of the virtual reference microphone (relative to the 'real' microphones of the hearing device) is termed the reference point. The hearing device (HD) comprises a BTE part adapted for being located at or in the external ear (pinna) of the user, and an ITE part adapted for being located at or in the ear canal of the user. The BTE-part comprises two (BTE1, BTE2) of the three microphones of the hearing device (HD). The ITE-part comprises the third microphone (ITE, here facing the environment). The three 'physical microphones (BTE1, BTE2, ITE) are indicated by solid (circular) dots. The (virtual) reference microphone is indicated by a dotted open circle between the two BTE-microphones (BTE1, BTE2).

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

REFERENCES

U.S. Pat. No. 7,471,798 B2. Microphone Array Having a Second Order Directional Pattern, D. M. Warren, Knowles Electronics, Published Feb. 5, 2004.
U.S. Pat. No. 9,301,049 B2. Noise-reducing Directional Microphone Array, G. W. Elko, M. Meyer, F. Gaensler, M H Acoustic LLC, Published Jan. 10, 2013.
EP3413589A1. "A microphone system and a hearing device comprising a microphone system". Oticon A/S. Published Jun. 6, 2018.
[Brandstein & Ward; 2001] M. Brandstein and D. Ward, "Microphone Arrays", Springer 2001.

The invention claimed is:

1. A hearing aid comprising:
at least two input transducers used to convert sound in an environment of the hearing aid to respective first and second electric input signals,
processing circuitry for establishing a primary adaptive 2-channel beamformer and a secondary adaptive 2-channel beamformer, each of the primary and secondary adaptive 2-channel beamformers providing an output signal for reducing noise in connection with a target direction based on first and second beamformer-input signals, said primary and secondary adaptive 2-channel beamformers being coupled in a cascaded structure such that:
said first and second beamformer-input signals of the primary adaptive 2-channel beamformer are the first and second electric input signals,
one of the first and second beamformer-input signals of the secondary adaptive 2-channel beamformer is the output signal of the primary adaptive 2-channel beamformer, and
the other of the first and second beamformer-input signals of the secondary adaptive 2-channel beamformer is an external audio input signal received via transceiver circuitry or an input signal from a third input transducer in the hearing aid,
wherein the output signal of the secondary adaptive 2-channel beamformer provides an estimate of a target signal.

2. A hearing aid according to claim 1 comprising an ITE part adapted for being located in or at the ear canal, and wherein the ITE part comprises an ITE-input transducer.

3. A hearing aid according to claim 1 comprising a processor configured to process said estimate of said target signal by applying a frequency and level dependent gain/attenuation according to the user's needs.

4. A hearing aid according to claim 1 wherein said hearing aid comprises an output transducer configured to provide stimuli perceivable as sound for the user based on said estimate of said target signal.

5. A hearing aid according to claim 1 wherein said primary or secondary adaptive 2-channel beamformers are minimum variance distortionless response (MVDR) beamformers.

6. A hearing aid according to claim 1 wherein said primary or secondary adaptive 2-channel beamformers are implemented by applying complex weights in a signal path with complex sub-band analysis/synthesis filter banks.

7. A hearing aid according to claim 6 wherein said complex weights are calculated based on a Generalized Sidelobe Canceller (GSC) structure comprising a target-adaptive omni-directional beamformer and a target cancelling beamformer and a noise-adaptive scalar $\beta$.

8. A hearing aid according to claim 1 wherein an adaptive parameter of said primary or secondary adaptive 2-channel beamformer is determined from the first and second beamformer-input signals for said first or second 2-channel beamformers, respectively.

9. A hearing aid according to claim 1 wherein said input transducers each comprise a microphone.

10. A hearing aid according to claim 1 comprising a BTE-part comprising two or three microphones.

11. A hearing aid according to claim 1 comprising a BTE-part comprising at least three microphones, which—when worn by the user—are located on a straight line as a linear array, or are located two and two on first, second, and third straight lines, which together form a triangle.

12. A hearing aid according to claim 1 being adapted to establish a communication link to an auxiliary device to provide that information or audio can be exchanged or forwarded from one to the other.

13. A hearing aid according to claim 12 wherein the auxiliary device comprises a user interface allowing the user to indicate a location of or a direction of arrival to a target sound source.

14. A hearing aid according to claim 12 wherein said auxiliary device comprises one or more of a remote control, a smartphone, a portable electronic device, a wearable electronic device, and a smartwatch.

15. A binaural hearing aid system comprising first and second hearing aids according to claim 1 and further comprising an auxiliary device, the binaural hearing aid system being adapted to establish a communication link between the first or second hearing aid and the auxiliary device to provide that information or audio can be exchanged or forwarded from one to the other.

16. A method of operating a hearing aid, where the hearing aid comprising:
at least two input transducers used to convert sound in an environment of the hearing aid to respective first and second electric input signals,
the method comprising
providing
a primary adaptive 2-channel beamformer,
a secondary adaptive 2-channel beamformer, and
that each of the primary and secondary adaptive 2-channel beamformers providing an output signal for reducing noise in connection with a target direction based on first and second beamformer-input signals, and
that said primary and secondary adaptive 2-channel beamformers are coupled in a cascaded structure configured to provide that:
said first and second beamformer-input signals of the primary adaptive 2-channel beamformer are the first and second electric input signals,
one of the first and second beamformer-input signals of the secondary adaptive 2-channel beamformer is the output signal of the primary 2-channel beamformer, and
the other of the first and second beamformer-input signals of the secondary adaptive 2-channel beamformer is an external audio input signal received via transceiver circuitry or an input signal from a third input transducer in the hearing aid,
wherein the output signal of the secondary adaptive 2-channel beamformer provides an estimate of a target signal.

* * * * *